United States Patent
Conklin et al.

(12) 
(10) Patent No.: US 6,756,214 B2
(45) Date of Patent: Jun. 29, 2004

(54) PROTEIN ZLMDA33

(75) Inventors: Darrell C. Conklin, Seattle, WA (US); Zeren Gao, Redmond, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 10/012,143

(22) Filed: Nov. 8, 2001

(65) Prior Publication Data

US 2003/0171540 A1 Sep. 11, 2003

Related U.S. Application Data

(60) Provisional application No. 60/247,538, filed on Nov. 9, 2000.

(51) Int. Cl.$^7$ .................. C12N 15/00; C12N 15/63; C12N 15/85; C07H 21/02; C07H 21/04
(52) U.S. Cl. .................. 435/69.1; 435/320.1; 435/325; 435/348; 435/252.3; 435/254.11; 536/23.1; 536/23.5
(58) Field of Search .................. 435/69.1, 320.1, 435/325, 348, 252.3, 254.11; 536/23.1, 23.5

(56) References Cited

FOREIGN PATENT DOCUMENTS

WO          WO99/53095          10/1999

OTHER PUBLICATIONS

Pineau, P., et al., *Journal of Viroloy*, 70(10):7280–7284, 1996.
GenBank Accession No. Z17856.
THC Z17856.
Schudy, A., Accession No. AF189745, 2000.
Pineau, P., Accession No. AJ222811.
GenBank Accession No. AI141514.
GenBank Accession No. AA904980.
GenBank Accession No. AA781133.
GenBank Accession No. AI184519.

*Primary Examiner*—Karen A. Canella
(74) *Attorney, Agent, or Firm*—Gary E. Parker; James M. Bogden

(57) ABSTRACT

Novel polypeptides, polynucleotides encoding them, materials and methods for making them, antibodies that specifically bind to them, and methods of using the polypeptides, polynucleotides, and antibodies are disclosed. The polypeptides comprise at least nine contiguous amino acid residues of SEQ ID NO:2 or SEQ ID NO:5, and may be prepared as polypeptide fusions comprising heterologous sequences, such as affinity tags. The polypeptides and polynucleotides encoding them may be used within a variety of therepeutic, diagnostic, and research applications, including in vitro diagnosis and in vivo imaging of cancers and other sites of abnormal cell proliferation.

9 Claims, 1 Drawing Sheet

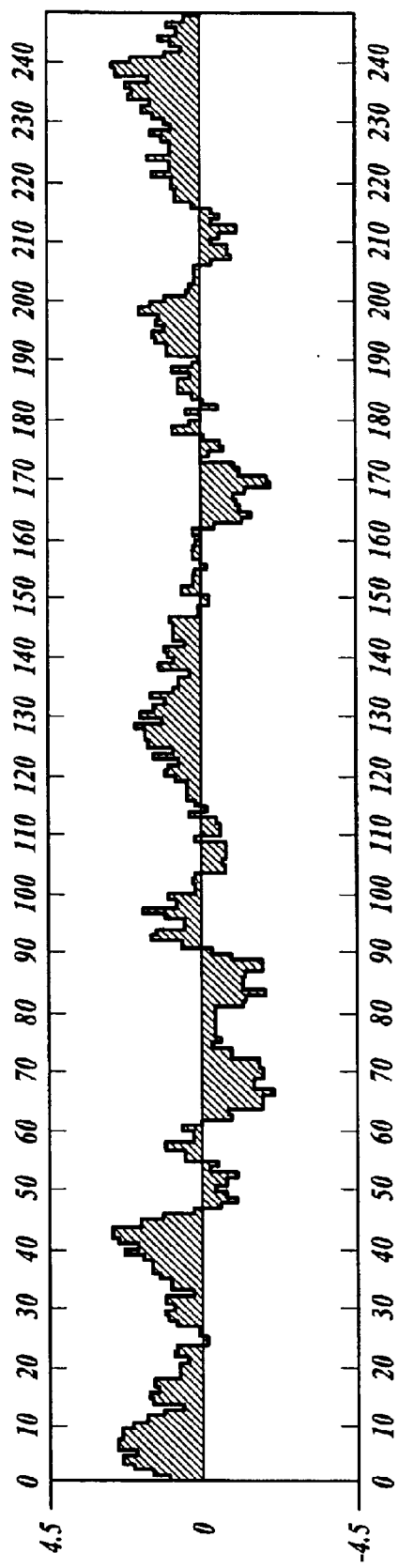

PROTEIN ZLMDA33

CROSS-REFERENCE TO RELATED APPLICATIONS

This application claims the benefit under 35 U.S.C. 119(e) of provisional application No. 60/247,538, filed Nov. 9, 2000.

BACKGROUND OF THE INVENTION

Expression of specific genes and production of the cognate encoded proteins within cells and tissues is dependent in part upon the metabolic state of the cell or tissue. Certain genes are expressed only at specific developmental stages, such as the fetal stage. A protein may be produced in one tissue during fetal development, and in another tissue during the adult stage. Other proteins may be produced during fetal development but not in normal adult tissue.

Genes may be expressed in abnormal amounts or abnormal locations in some pathological states, particularly in cancers. Gene expression and protein production are therefore indicators of the metabolic state of cells and tissues. For example, production of a particular protein in a certain tissue may be indicative of a cancerous or pre-cancerous state. Cancer-specific proteins may also be released by cells into bodily fluids, where they can be detected by conventional diagnostic methods.

Cancer-specific gene expression also provides targets for therapeutic intervention. By reducing or blocking such gene expression or by interfering in the biological activity of the encoded protein, tumor development may be slowed or reversed. Tumor-specific proteins also provide targets for the delivery of therapeutic agents, providing for more specific treatment with reduced side effects.

DESCRIPTION OF THE INVENTION

Within one aspect of the invention there is provided an isolated polypeptide comprising at least nine contiguous amino acid residues of SEQ ID NO:2 or SEQ ID NO:5. Within one embodiment, the isolated polypeptide consists of from 15 to 1500 amino acid residues. Within another embodiment, the at least nine contiguous amino acid residues of SEQ ID NO:2 or SEQ ID NO:5 are operably linked via a peptide bond or polypeptide linker to a second polypeptide selected from the group consisting of maltose binding protein, an immunoglobulin constant region, a poly-histidine tag, and a peptide as shown in SEQ ID NO:3. Within another embodiment, the isolated polypeptide comprises at least 30 contiguous residues of SEQ ID NO:2 or SEQ ID NO:5. Exemplary polypeptides of the invention include, without limitation, those comprising residues 2–8, 15–22, 38–45, 94–99, 110–115, 196–202, 215–220, 235–241, 2–22, 110–133, 120–133, 121–132, 192–203, 214–226, or 214–242 SEQ ID NO:2.

Within a second aspect of the invention there is provided an expression vector comprising the following operably linked elements: a transcription promoter, a DNA segment encoding a protein comprising residues 1–248 of SEQ ID NO:2 or SEQ ID NO:5, and a transcription terminator. Within one embodiment, the DNA segment comprises nucleotides 174–917 of SEQ ID NO:1. Within another embodiment, the expression vector further comprises a secretory signal sequence operably linked to the DNA segment.

Within a third aspect of the invention there is provided a cultured cell into which has been introduced an expression vector as disclosed above, wherein the cell expresses the DNA segment. Within one embodiment, the expression vector comprises a secretory signal sequence operably linked to the DNA segment, and the protein is secreted by the cell. The cultured cell of the invention can be used, inter alia, within a method of making a protein, wherein the cell is cultured under conditions whereby the DNA segment is expressed and the protein is produced, and the protein is recovered. Within one embodiment, the expression vector comprises a secretory signal sequence operably linked to the DNA segment, the protein is secreted by the cell, and the protein is recovered from a medium in which the cell is cultured.

Within a fourth aspect of the invention there is provided a protein produced by the method disclosed above.

Within a fifth aspect of the invention there is provided an antibody that specifically binds to a protein as disclosed above. Within one embodiment of the invention the antibody is labeled to produce a detectable signal.

Within a sixth aspect of the invention there is provided a method of detecting, in a test sample, a polypeptide selected from the group consisting of (a) a polypeptide as shown in SEQ ID NO:2, (b) a polypeptide as shown in SEQ ID NO:5, and (c) proteolytic fragments of (a) or (b). The method comprises combining the test sample with an antibody as disclosed above under conditions whereby the antibody binds to the polypeptide, and detecting the presence of antibody bound to the polypeptide.

Within a seventh aspect of the invention there are provided isolated polynucleotides encoding the polypeptides disclosed above. Within one aspect of the invention the isolated polynucleotide comprises nucleotides 1–744 of SEQ ID NO:4 or SEQ ID NO:6. Within another aspect of the invention the isolated polynucleotide comprises nucleotides 174–917 of SEQ ID NO:1.

These and other aspects of the invention will become evident upon reference to the following detailed description of the invention and the accompanying FIGURE.

The FIGURE is a Kyte-Doolittle hydrophilicity profile of the amino acid sequence shown in SEQ ID NO:2. The profile was prepared using Protean™ 3.14 (DNAStar, Madison, Wis.).

Prior to setting forth the invention in detail, it may be helpful to the understanding thereof to define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J*. 4:1075, 1985; Nilsson et al., *Methods Enzymol*. 198:3, 1991), glutathione S transferase (Smith and Johnson, *Gene* 67:31, 1988), Glu—Glu affinity tag (Grussenmeyer et al., *Proc. Natl. Acad. Sci. USA* 82:7952-4, 1985) (SEQ ID NO:3), substance P, Flag™ peptide (Hopp et al., *Biotechnology* 6:1204–1210, 1988), streptavidin binding peptide, maltose binding protein (Guan et al., *Gene* 67:21–30, 1987), cellulose binding protein, thioredoxin, ubiquitin, T7 polymerase, or other antigenic epitope or binding domain. See, in general, Ford et al., *Protein Expression and Purification* 2: 95–107, 1991. DNAs encoding affinity tags and other reagents are available from commercial suppliers (e.g., Pharmacia Biotech, Piscataway, N.J.; New England Biolabs, Beverly, Mass.; Eastman Kodak, New Haven, Conn.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequences. The term allelic variant is also used herein to denote a polypeptide encoded by an allelic variant of a gene.

A "complement" of a polynucleotide molecule is a polynucleotide molecule having a complementary base sequence and reverse orientation as compared to a reference sequence. For example, the sequence 5' ATGCACGGG 3' is complementary to 5' CCCGTGCAT 3'.

"Conservative amino acid substitutions" are defined by the BLOSUM62 scoring matrix of Henikoff and Henikoff, *Proc. Natl. Acad. Sci. USA* 89:10915–10919, 1992, an amino acid substitution matrix derived from about 2,000 local multiple alignments of protein sequence segments, representing highly conserved regions of more than 500 groups of related proteins. As used herein, the term "conservative amino acid substitution" refers to a substitution represented by a BLOSUM62 value of greater than –1. For example, an amino acid substitution is conservative if the substitution is characterized by a BLOSUM62 value of 0, 1, 2, or 3. Preferred conservative amino acid substitutions are characterized by a BLOSUM62 value of at least one 1 (e.g., 1, 2 or 3), while more preferred conservative amino acid substitutions are characterized by a BLOSUM62 value of at least 2 (e.g., 2 or 3).

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

An "inhibitory polynucleotide" is a DNA or RNA molecule that reduces or prevents expression (transcription or translation) of a second (target) polynucleotide. Inhibitory polynucleotides include anti sense polynucleotides, ribozymes, and external guide sequences. The term "inhibitory polynucleotide" further includes DNA and RNA molecules that encode the actual inhibitory species, such as DNA molecules that encode ribozymes.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. The isolated polypeptide or protein may be prepared substantially free of other polypeptides or proteins, particularly those of animal origin. For some purposes, the polypeptides and proteins will be prepared in a highly purified form, i.e. greater than 95% pure or greater than 99% pure. When used in this context, the term "isolated" does not exclude the presence of the same polypeptide or protein in alternative physical forms, such as dimers or alternatively glycosylated or derivatized forms.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function (s) of the sequences are retained.

The term "ortholog" denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When these terms are applied to double-stranded molecules they are used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless. Thus, a protein "consisting of", for example, from 15 to 1500 amino acid residues may further contain one or more carbohydrate chains.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

All references cited herein are incorporated by reference in their entirety.

The present invention is based on the discovery of a novel polynucleotide and protein encoded by the polynucleotide. The polynucleotide is expressed primarily in fetal brain, spinal cord, testis prostate smooth muscle cells, thyroid, bone marrow, uterine tumor, and ovarian tumor, and is not expressed in many other tissues and cells, including normal uterus and normal ovary. The polynucleotide and protein are thus markers for uterine and ovarian tumors in a mammal, and also provide targets for diagnostic and therapeutic agents. This novel protein is termed "zlmda33."

A representative human zlmda33 DNA sequence is shown in SEQ ID NO:1, and the encoded amino acid sequence is shown in SEQ ID NO:2. The human protein comprises 248 amino acid residues. It does not appear to contain a secretory peptide, and is therefore believed to be an intracellular protein. Those skilled in the art will recognize that SEQ ID NO:1 and SEQ ID NO:2 represent a single allele of zlmda33, and that allelic variation is expected to exist. A second human zlmda33 protein is shown in SEQ ID NO:5, which differs from SEQ ID NO:2 at residues 85 and 111. Those skilled in the art will also recognize that many proteins are produced in alternatively spliced forms.

Polypeptides of the present invention comprise at least 9 or at least 15 contiguous amino acid residues of SEQ ID NO:2 or SEQ ID NO:5. Within certain embodiments of the invention, the polypeptides comprise 20, 30, 40, 50, 100, or more contiguous residues of SEQ ID NO:2 or SEQ ID NO:5, up to the entire primary translation product (residues 1 to 248 of SEQ ID NO:2 or SEQ ID NO:5). As disclosed in more detail below, these polypeptides can further comprise additional, non-zlmda33, polypeptide sequence(s).

Within the polypeptides of the present invention are polypeptides that comprise an epitope-bearing portion of a protein as shown in SEQ ID NO:2 or SEQ ID NO:5. An "epitope" is a region of a protein to which an antibody can bind. See, for example, Geysen et al., *Proc. Natl. Acad. Sci. USA* 81:3998–4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660–666, 1983. Antibodies that recognize short, linear epitopes are particularly useful in analytic and diagnostic applications that employ denatured protein, such as Western blotting (Tobin, *Proc. Natl. Acad. Sci. USA* 76:4350–4356, 1979), or in the analysis of fixed cells or tissue samples. Antibodies to linear epitopes are also useful for detecting fragments of zlmda33, such as might occur in body fluids or cell culture media.

Antigenic, epitope-bearing polypeptides of the present invention are useful for raising antibodies, including monoclonal antibodies, that specifically bind to a zlmda33 protein. Antigenic, epitope-bearing polypeptides contain a sequence of at least six, generally at least nine, often from 15 to about 30 contiguous amino acid residues of a zlmda33 protein (e.g., SEQ ID NO:2). Polypeptides comprising a larger portion of a zlmda33 protein, i.e. from 30 to 50 residues up to the entire sequence, are included. It is preferred that the amino acid sequence of the epitope-bearing polypeptide is selected to provide substantial solubility in aqueous solvents, that is the sequence includes relatively hydrophilic residues, and hydrophobic residues are substantially avoided. Such regions include those comprising residues 2–8, 15–22, 38–45, 94–99, 110–115, 121–132, 196–202, 215–220, and 235–241 of SEQ ID NO:2. Larger hydrophilic peptides include, for example, residues 2–22, 110–133, 120–133, 192–203, 214–226, and 214–242.

Polypeptides of the present invention can be prepared with one or more amino acid substitutions, deletions or additions as compared to SEQ ID NO:2 or SEQ ID NO:5. These changes are preferably of a minor nature, such as conservative amino acid substitutions and other changes that do not significantly affect the folding or activity of the protein or polypeptide. Other exemplary changes include amino- or carboxyl-terminal extensions, such as an amino-terminal methionine residue, an amino or carboxyl-terminal cysteine residue to facilitate subsequent linking to maleimide-activated keyhole limpet hemocyanin, a small linker peptide of up to about 20–25 residues, or an extension that facilitates purification (an affinity tag) as disclosed above. Two or more affinity tags may be used in combination. Polypeptides comprising affinity tags can further comprise a polypeptide linker and/or a proteolytic cleavage site between the zlmda33 polypeptide and the affinity tag. Such cleavage sites include, for example, thrombin cleavage sites and factor Xa cleavage sites.

The present invention further provides a variety of other polypeptide fusions. For example, a zlmda33 polypeptide can be prepared as a fusion to a dimerizing protein as disclosed in U.S. Pat. Nos. 5,155,027 and 5,567,584. Dimerizing proteins in this regard include, for example, immunoglobulin fragments comprising constant region and hinge domains. For example, a zlmda33 polypeptide can be joined to an IgG Fc fragment (consisting essentially of $C_H2$, $C_H3$, and hinge). Such fusions are typically secreted as multimeric molecules wherein the Fc portions are disulfide bonded to each other and the two non-Ig polypeptides are arrayed in close proximity to each other. Dimerization can also be stabilized by fusing a zlmda33 polypeptide to a leucine zipper sequence (Riley et al., *Protein Eng.* 9:223–230, 1996; Mohamed et al., *J. Steroid Biochem. Mol. Biol.* 51:241–250, 1994). Immunoglobulin-zlmda33 polypeptide fusions and leucine zipper fusions can be expressed in genetically engineered cells to produce a variety of multimeric zlmda33 analogs. Auxiliary domains can be fused to zlmda33 polypeptides to target them to specific cells, tissues, or macromolecules (e.g., collagen). For example, a zlmda33 polypeptide or protein can be targeted to a predetermined cell type by fusing a zlmda33 polypeptide to a ligand that specifically binds to a receptor on the surface of the target cell. In this way, polypeptides and proteins can be targeted for therapeutic or diagnostic purposes. A zlmda33 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996. Within immunoglobulin-zlmda33 fusion proteins, certain amino acid subsititutions may be introduced into the Ig portion to alter effector functions associated with the native Ig. For example, amino acid substitutions can be made at EU index positions 234, 235, and 237 to reduce binding to FcγRI, and at EU index positions 330 and 331 to reduce complement fixation. See, Duncan et al., *Nature* 332:563–564, 1988; Winter et al., U.S. Pat. No. 5,624,821; Tao et al., *J. Exp. Med.* 178:661, 1993; and Canfield and Morrison, *J. Exp. Med.* 173:1483, 1991. The carboxyl-terminal lysine residue can be removed from the $C_H3$ domain to increase homogeneity of the product. Within fusions to an Ig heavy chain polypeptide, the Cys residue within the hinge region that is ordinarily disulfide-bonded to the light chain can be replaced with another amino acid residue, such as a serine residue, if the Ig fusion is not co-expressed with a light chain polypeptide. However, an Ig-zlmda33 fusion polypeptide can be co-expressed with a wild-type or fused light chain polypeptide as disclosed in U.S. Pat. No. 6,018,026. In addition, a zlmda33 polypeptide can be joined to another bioactive molecule, such as a cytokine, to provide a multi-functional molecule.

Polypeptide fusions of the present invention will generally contain not more than about 1,500 amino acid residues, usually not more than about 1,300 residues, more commonly not more than about 1,000 residues, and will in many cases be considerably smaller. For example, a zlmda33 polypeptide of 248 residues (e.g., residues 1–248 of SEQ ID NO:2) can be fused to *E. coli* β-galactosidase (1,021 residues; see Casadaban et al., *J. Bacteriol.* 143:971–980, 1980), a 10-residue spacer, and a 4-residue factor Xa cleavage site to yield a polypeptide of 1,283 residues. In a second example, residues 1–248 of SEQ ID NO:2 can be fused to maltose binding protein (approximately 370 residues), a 4-residue cleavage site, and a 6-residue polyhistidine tag.

The proteins of the present invention can also comprise non-naturally occuring amino acid residues. Non-naturally occuring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occuring amino acid residues into proteins. For example, an in vitro system can be employed wherein nonsense mutations are suppressed using chemically aminoacylated suppressor tRNAs. Methods for synthesizing amino acids and aminoacylating tRNAs are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occuring amino acid(s) (e.g., 2-azaphenylalanine, 3-azaphenylalanine, 4-azaphenylalanine, or 4-fluorophenylalanine). The non-naturally occuring amino acid is incorporated into the protein in place of its natural counterpart. See, Koide et al., *Biochem.* 33:7470–7476, 1994. Naturally occuring amino acid residues can be converted to non-naturally occuring species by in vitro chemical modification. Chemical modification can be combined with site-directed mutagenesis to further expand the range of substitutions (Wynn and Richards, *Protein Sci.* 2:395–403, 1993).

Amino acid sequence changes are made in zlmda33 polypeptides so as to minimize disruption of higher order structure essential to biological activity. Amino acid residues that are within regions or domains that are critical to maintaining structural integrity can be determined. Within these regions one can identify specific residues that will be more or less tolerant of change and maintain the overall tertiary structure of the molecule. Methods for analyzing sequence structure include, but are not limited to, alignment of multiple sequences with high amino acid or nucleotide identity, secondary structure propensities, binary patterns, complementary packing, and buried polar interactions (Barton, *Current Opin. Struct. Biol.* 5:372–376, 1995 and Cordes et al., *Current Opin. Struct. Biol.* 6:3–10, 1996). In general, determination of structure will be accompanied by evaluation of activity of modified molecules. The effects of amino acid sequence changes can be predicted by, for example, computer modeling using available software (e.g., the Insight II® viewer and homology modeling tools; MSI, San Diego, Calif.) or determined by analysis of crystal structure (see, e.g., Lapthorn et al, *Nature* 369:455–461, 1994; Lapthorn et al., *Nat. Struct. Biol.* 2:266–268, 1995). Protein folding can be measured by circular dichroism (CD). Measuring and comparing the CD spectra generated by a modified molecule and standard molecule are routine in the art (Johnson, *Proteins* 7:205–214, 1990). Crystallography is another well-known and accepted method for analyzing folding and structure. Nuclear magnetic resonance (NMR), digestive peptide mapping and epitope mapping are other known methods for analyzing folding and structural similarities between proteins and polypeptides (Schaanan et al., *Science* 257:961–964, 1992). Mass spectrometry and chemical modification using reduction and alkylation can be used to identify cysteine residues that are associated with disulfide bonds or are free of such associations (Bean et al., *Anal. Biochem.* 201:216–226, 1992; Gray, *Protein Sci.* 2:1732–1748, 1993; and Patterson et al., *Anal. Chem.* 66:3727–3732, 1994). Alterations in disulfide bonding will be expected to affect protein folding. These techniques can be employed individually or in combination to analyze and compare the structural features that affect folding of a variant protein or polypeptide to a standard molecule to determine whether such modifications would be significant.

A hydrophilicity profile of SEQ ID NO:2 is shown in the attached figure. Those skilled in the art will recognize that hydrophilicity will be taken into account when designing alterations in the amino acid sequence of a zlmda33 polypeptide, so as not to disrupt the overall profile.

Essential amino acids in the polypeptides of the present invention can be identified experimentally according to procedures known in the art, such as site-directed mutagenesis or alanine-scanning mutagenesis (Cunningham and Wells, *Science* 244, 1081–1085, 1989; Bass et al., *Proc. Natl. Acad. Sci. USA* 88:4498–4502, 1991). In the latter technique, single alanine mutations are introduced throughout the molecule, and the resultant mutant molecules are tested for biological activity as disclosed below to identify amino acid residues that are critical to the activity of the molecule.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). These authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zlmda33 DNA and polypeptide sequences can be generated through DNA shuffling as disclosed by Stemmer, *Nature* 370:389–391, 1994 and Stemmer, *Proc. Natl. Acad. Sci. USA* 91:10747–10751, 1994. Briefly, variant genes are generated by in vitro homologous recombination by random fragmentation of a parent gene followed by reassembly using PCR, resulting in randomly introduced point mutations. This technique can be modified by using a family of parent genes, such as allelic variants or genes from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

In many cases, the structure of the final polypeptide product will result from processing of the nascent polypeptide chain by the host cell, thus the final sequence of a zlmda33 polypeptide produced by a host cell will not always correspond to the full sequence encoded by the expressed polynucleotide. Such processing events include, for example, proteolysis, carbohydrate addition, and amino acid side chain modification. Differential processing of individual chains may result in heterogeneity of expressed polypeptides.

Mutagenesis methods as disclosed above can be combined with high volume or high-throughput screening methods to detect biological activity of zlmda33 variant polypeptides. Assays that can be scaled up for high throughput include mitogenesis assays, which can be run in a 96-well format. Mutagenized DNA molecules that encode active zlmda33 polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptide fragments or variants of SEQ ID NO:2 or SEQ ID NO:5 that retain the activity of wild-type zlmda33.

The present invention also provides zlmda33 polynucleotide molecules. These polynucleotides include DNA and RNA, both single- and double-stranded, the former encompassing both the sense strand and the antisense strand. A representative DNA sequence encoding the amino acid sequence of SEQ ID NO:2 is shown in SEQ ID NO:1. Those skilled in the art will readily recognize that, in view of the degeneracy of the genetic code, considerable sequence variation is possible among these polynucleotide molecules. SEQ ID NO:4 is a degenerate DNA sequence that encompasses all DNAs that encode the zlmda33 polypeptide of SEQ ID NO:2. SEQ ID NO:6 is a degenerate DNA sequence that encompasses all DNAs that encode the zlmda33 polypeptide of SEQ ID NO:5. Those skilled in the art will recognize that the degenerate sequences of SEQ ID NO:4 and SEQ ID NO:6 also provides all RNA sequences encoding SEQ ID NO:2 and SEQ ID NO:5, respectively, by substituting U for T. Thus, zlmda33 polypeptide-encoding polynucleotides comprising nucleotides 1–744 of SEQ ID NO:4, SEQ ID NO:6, and their RNA equivalents are contemplated by the present invention, as are segments of SEQ ID NO:4 and SEQ ID NO:6 encoding other zlmda33 polypeptides disclosed herein. Table 1 sets forth the one-letter codes used within SEQ ID NO:4 and SEQ ID NO:6 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:4 and SEQ ID NO:6, encompassing all possible codons for a given amino acid, are set forth in Table 2, below.

TABLE 2

| Amino Acid | One-Letter Code | Codons | | | | | | Degenerate Codon |
|---|---|---|---|---|---|---|---|---|
| Cys | C | TGC | TGT | | | | | TGY |
| Ser | S | AGC | AGT | TCA | TCC | TCG | TCT | WSN |
| Thr | T | ACA | ACC | ACG | ACT | | | CAN |
| Pro | P | CCA | CCC | CCG | CCT | | | CCN |
| Ala | A | GCA | GCC | GCG | GCT | | | GCN |

TABLE 2-continued

| Amino Acid | One-Letter Code | Codons | Degenerate Codon |
|---|---|---|---|
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |
| Gap | – | – | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by a degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit preferential codon usage. See, in general, Grantham et al., *Nuc. Acids Res.* 8:1893–1912, 1980; Haas et al. *Curr. Biol.* 6:315–324, 1996; Wain-Hobson et al., *Gene* 13:355–364, 1981; Grosjean and Fiers, *Gene* 18:199–209, 1982; Holm, *Nuc. Acids Res.* 14:3075–3087, 1986; and Ikemura, *J. Mol. Biol.* 158:573–597, 1982. Introduction of preferred codon sequences into recombinant DNA can, for example, enhance production of the protein by making protein translation more efficient within a particular cell type or species. Therefore, the degenerate codon sequence disclosed in SEQ ID NO:4 serves as a template for optimizing expression of polynucleotides in various cell types and species commonly used in the art and disclosed herein.

Within certain embodiments of the invention the isolated polynucleotides will hybridize to similar sized regions of SEQ ID NO:1 or a sequence complementary thereto under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for preparing DNA and RNA are well known in the art. In general, RNA is isolated from a tissue or cell that produces large amounts of zlmda33 RNA. Cells from testis, spinal cord, fetal brain, ovarian tumor, and uterine tumor are preferred. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly(A)$^+$ RNA using known methods. In the alternative, genomic DNA can be isolated. Polynucleotides encoding zlmda33 polypeptides are then identified and isolated by, for example, hybridization or PCR.

Full-length clones encoding zlmda33 can be obtained by conventional cloning procedures. Complementary DNA (cDNA) clones are usually preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zlmda33, receptor fragments, or other specific binding partners.

Zlmda33 polynucleotide sequences disclosed herein can also be used as probes or primers to clone 5' non-coding regions of a zlmda33 gene. Promoter elements from a zlmda33 gene can be used to direct the expression of heterologous genes in, for example, transgenic animals or patients treated with gene therapy. Cloning of 5' flanking sequences also facilitates production of zlmda33 proteins by "gene activation" as disclosed in U.S. Pat. No. 5,641,670. Briefly, expression of an endogenous zlmda33 gene in a cell is altered by introducing into the zlmda33 locus a DNA construct comprising at least a targeting sequence, a regulatory sequence, an exon, and an unpaired splice donor site. The targeting sequence is a zlmda33 5' non-coding sequence that permits homologous recombination of the construct with the endogenous zlmda33 locus, whereby the sequences within the construct become operably linked with the endogenous zlmda33 coding sequence. In this way, an endogenous zlmda33 promoter can be replaced or supplemented with other regulatory sequences to provide enhanced, tissue-specific, or otherwise regulated expression. A portion of the zlmda33 gene, including a large 5' non-coding region, is available as GenBank accession number AF189745.

Those skilled in the art will recognize that the sequences disclosed in SEQ ID NOS:1 and 2 represent a single allele of human zlmda33. Allelic variants of these sequences can be cloned by probing cDNA or genomic libraries from different individuals according to standard procedures.

The present invention further provides counterpart polypeptides and polynucleotides from other species ("orthologs"). Of particular interest are zlmda33 polypeptides from other mammalian species, including murine, porcine, ovine, bovine, canine, feline, equine, and other primate polypeptides. These non-human zlmda33 polypeptides and polynucleotides, as well as antagonists thereof and other related molecules, can be used, inter alia, in veterinary medicine. Orthologs of human zlmda33 can be cloned using information and compositions provided by the present invention in combination with conventional cloning techniques. For example, a cDNA can be cloned using mRNA obtained from a tissue or cell type that expresses zlmda33 as disclosed above. A library is then prepared from mRNA of a positive tissue or cell line. A zlmda33-encoding cDNA can then be isolated by a variety of methods, such as by probing with a complete or partial human cDNA or with one or more sets of degenerate probes based on the disclosed sequence. A cDNA can also be cloned using the polymerase chain reaction, or PCR (Mullis, U.S. Pat. No. 4,683,202), using primers designed from the representative human zlmda33 sequence disclosed herein. Within an additional method, a cDNA library can be used to transform or transfect host cells, and expression of the cDNA of interest can be detected with an antibody to zlmda33 polypeptide. Similar techniques can also be applied to the isolation of genomic clones.

For any zlmda33 polypeptide, including variants and fusion proteins, one of ordinary skill in the art can readily generate a fully degenerate polynucleotide sequence encoding that variant using the information set forth in Tables 1 and 2, above. Moreover, those of skill in the art can use standard software to devise zlmda33 variants based upon the nucleotide and amino acid sequences described herein. The present invention thus provides a computer-readable medium encoded with a data structure that provides at least one of the following sequences: SEQ ID NO:1, SEQ ID NO:2, SEQ ID NO:4, SEQ ID NO:5, and portions thereof. Suitable forms of computer-readable media include, without limitation, a hard or fixed drive, a random access memory (RAM) chip, a floppy disk, digital linear tape (DLT), a disk cache, a ZIP™ disk, compact discs (e.g., CD-read only memory (ROM), CD-rewritable (RW), and CD-recordable), digital versatile/video discs (DVD) (e.g., DVD-ROM, DVD-RAM, and DVD+RW), and carrier waves.

The zlmda33 polypeptides of the present invention, including full-length polypeptides, biologically active fragments, and fusion polypeptides can be produced according to conventional techniques using cells into which have been introduced an expression vector encoding the polypeptide. As used herein, "cells into which have been introduced an expression vector" include both cells that have been directly manipulated by the introduction of exogenous DNA molecules and progeny thereof that contain the introduced DNA. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zlmda33 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers can be provided on separate vectors, and replication of the exogenous DNA is provided by integration into the host cell genome. Selection of promoters, terminators, selectable markers, vectors and other elements is a matter of routine design within the level of ordinary skill in the art. Many such elements are described in the literature and are available through commercial suppliers.

To direct a zlmda33 polypeptide into the secretory pathway of a host cell, a secretory signal sequence (also known as a leader sequence, prepro sequence or pre sequence) is provided in the expression vector. The secretory signal sequence may be derived from another secreted protein (e.g., t-PA; see, U.S. Pat. No. 5,641,655) or synthesized de novo. The secretory signal sequence is operably linked to the zlmda33 DNA sequence, i.e., the two sequences are joined in the correct reading frame and positioned to direct the newly sythesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells can be used as hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1, ATCC No. CCL 61; or CHO DG44, Chasin et al., *Som. Cell. Molec. Genet.* 12:555, 1986) cell lines. Additional suitable cell lines are known in the art and available from public depositories such as the American Type Culture Collection, Manassas, Va. Suitable promoters include those from metallothionein genes (U.S. Pat. Nos. 4,579,821 and 4,601,978), the adenovirus major late promoter, and promoters from SV-40 or cytomegalovirus. See, e.g., U.S. Pat. Nos. 4,579,821; 4,601, 978; and 4,956,288. Expression vectors for use in mammalian cells include pZP-1 and pZP-9, which have been deposited with the American Type Culture Collection, Manassas, Va. USA under accession numbers 98669 and 98668, respectively, and derivatives thereof.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that produce an altered phenotype, such as green fluorescent protein, or cell surface proteins such as CD4, CD8, Class I MHC, and placental alkaline phosphatase, can be used to sort transfected cells from untransfected cells by such means as FACS or magnetic bead separation technology.

The adenovirus system (disclosed in more detail below) can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. In an alternative method, adenovirus vector-infected 293 cells can be grown as adherent cells or in suspension culture at relatively high cell density to produce significant amounts of protein (See Gamier et al., *Cytotechnol*. 15:145–55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins can also be effectively obtained.

Insect cells can be infected with recombinant baculovirus, commonly derived from *Autographa californica* nuclear polyhedrosis virus (AcNPV) according to methods known in the art, such as the transposon-based system described by Luckow et al. (*J. Virol.* 67:4566–4579, 1993). This system, which utilizes transfer vectors, is commercially available in kit form (Bac-to-Ba™ kit; Life Technologies, Rockville, Md.). The transfer vector (e.g., pFastBac1™; Life Technologies) contains a Tn7 transposon to move the DNA encoding the protein of interest into a baculovirus genome maintained in *E. coli* as a large plasmid called a "bacmid." See, Hill-Perkins and Possee, *J. Gen. Virol.* 71:971–976, 1990; Bonning et al., *J. Gen. Virol.* 75:1551–1556, 1994; and Chazenbalk and Rapoport, *J. Biol. Chem.* 270:1543–1549, 1995. In addition, transfer vectors can include an in-frame fusion with DNA encoding a polypeptide extension or affinity tag as disclosed above. Using techniques known in the art, a transfer vector containing a zlmda33-encoding sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses zlmda33 protein is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., High Five™ cells; Invitrogen, Carlsbad, Calif.). See, for example, U.S. Pat. No. 5,300,435. Serum-free media are used to grow and maintain the cells. Suitable media formulations are known in the art and can be obtained from commercial suppliers. The cells are grown up from an inoculation density of approximately $2-5\times10^5$ cells to a density of $1-2\times10^6$ cells, at which time a recombinant viral stock is added at a multiplicity of infection (MOI) of 0.1 to 10, more typically near 3. Procedures used are generally known in the art.

Other higher eukaryotic cells can also be used as hosts, including plant cells and avian cells. The use of *Agrobacterium rhizogenes* as a vector for expressing genes in plant cells has been reviewed by Sinkar et al., *J. Biosci.* (*Bangalore*) 11:47–58, 1987.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, 1986; Cregg, U.S. Pat. No. 4,882,279; and Raymond et al., *Yeast* 14 11–23, 1998. Aspergillus cells can be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533. Production of recombinant proteins in *Pichia methanolica* is disclosed in U.S. Pat. Nos. 5,716,808, 5,736,383, 5,854,039, and 5,888,768.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zlmda33 polypeptide in bacteria such as *E. coli*, the polypeptide may be retained in the cytoplasm or may be directed to the periplasmic space by a bacterial secretion sequence. In the former case the cells are lysed, and the zlmda33 polypeptide is recovered from the lysate. If the polypeptide is present in the cytoplasm as insoluble granules, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and re covering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. Liquid cultures are provided with sufficient aeration by conventional means, such as shaking of small flasks or sparging of fermentors.

Zlmda33 polypeptides can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989. In vitro synthesis is particularly advantageous for the preparation of smaller polypeptides.

Using methods known in the art, zlmda33 proteins can be prepared as monomers or multimers; glycosylated or non-glycosylated; pegylated or non-pegylated; and may or may not include an initial methionine amino acid residue. In many cases, the structure of the final protein will result from processing of the nascent polypeptide chain by the host cell, thus the final sequence of a zlmda33 polypeptide produced by a host cell will not always correspond to the full sequence encoded by the expressed polynucleotide. Differential processing of individual chains may result in heterogeneity of expressed proteins.

Depending upon the intended use, the polypeptides and proteins of the present invention can be purified to ≧80% purity, ≧90% purity, ≧95% purity, or to a pharmaceutically pure state, that is greater than 99.9% pure with respect to contaminating macromolecules, particularly other proteins and nucleic acids, and free of infectious and pyrogenic agents. Within certain embodiments, the polypeptide or protein is substantially free of other polypeptides or proteins, particularly those of animal origin.

Zlmda33 proteins (including chimeric polypeptides and multimeric proteins) are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321–1325, 1988. Proteins comprising a glu—glu tag can be purified by immunoaffinity chromatography according to conventional procedures. See, for example, Grussenmeyer et al., ibid. Maltose binding protein fusions are purified on an amylose column according to methods known in the art.

Biological activities of zlmda33 proteins can be measured in vitro using cultured cells or in vivo by administering molecules of the claimed invention to the appropriate animal model. Many such assays and models are known in the art. Guidance in initial assay selection is provided by structural predictions and sequence alignments. However, even if no functional prediction is made, the activity of a protein can be elucidated by known methods, including, for example, screening a variety of target cells for a biological response, other in vitro assays, expression in a host animal, or through the use of transgenic and/or "knockout" animals. Through the application of robotics, many in vitro assays can be adapted to rapid, high-throughput screeing of a large number of samples.

The activity of zlmda33 proteins can be measured with a silicon-based biosensor microphysiometer that measures the extracellular acidification rate or proton excretion associated with receptor binding and subsequent physiologic cellular responses. An exemplary such device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell et al., *Science* 257:1906–1912, 1992; Pitchford et al., *Meth. Enzymol.* 228:84–108, 1997; Arimilli et al., *J. Immunol. Meth.* 212:49–59, 1998; and Van Liefde et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including zlmda33 proteins, their agonists, and antagonists.

Assays measuring cell proliferation or differentiation are well known in the art. For example, assays measuring proliferation include such assays as chemosensitivity to neutral red dye (Cavanaugh et al., *Investigational New Drugs* 8:347–354, 1990), incorporation of radiolabeled nucleotides (as disclosed by, e.g., Raines and Ross, *Methods Enzymol.* 109:749–773, 1985; Wahl et al., *Mol. Cell Biol.* 8:5016–5025, 1988; and Cook et al., *Analytical Biochem.* 179:1–7, 1989), incorporation of 5-bromo-2'-deoxyuridine (BrdU) in the DNA of proliferating cells (Porstmann et al., *J. Immunol. Methods* 82:169–179, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988). Differentiation can be assayed using suitable precursor cells that can be induced to differentiate into a more mature phenotype. Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; and Raes, *Adv. Anim. Cell Biol. Technol. Bioprocesses,* 161–171, 1989). Effects of a protein on tumor cell growth and metastasis can be analyzed using the Lewis lung carcinoma model, for example as described by Cao et al., *J. Exp. Med.* 182:2069–2077, 1995.

Activity of a protein on cells of neural origin can be analyzed using assays that measure effects on neurite growth as disclosed below.

Zlmda33 activity may also be detected using assays designed to measure zlmda33 modulation of production of one or more additional growth factors or other macromolecules. Such assays include those for determining the presence of hepatocyte growth factor (HGF), epidermal growth factor (EGF), transforming growth factor alpha (TGFα), interleukin-6 (IL-6), VEGF, acidic fibroblast growth factor (aFGF), angiogenin, and other macromolecules. Assays of IL-1 activity include, for example, gel-shift assays for NF-κB activation, Thr-669 kinase activity assays, and IL-8 promoter activation assays. See, Mitcham et al., *J. Biol. Chem.* 271:5777–5783, 1996. Suitable assays include mitogenesis assays, receptor-binding assays, competition binding assays, immunological assays (e.g., ELISA), and other formats known in the art. Metalloprotease secretion is measured from treated primary human dermal fibroblasts, synoviocytes and chondrocytes. The relative levels of collagenase, gelatinase and stromalysin produced in response to culturing in the presence of a zlmda33 protein is measured using zymogram gels (Loita and Stetler-Stevenson, *Cancer Biology* 1:96–106, 1990). Procollagen/collagen synthesis by dermal fibroblasts and chondrocytes in response to a test protein is measured using $^3$H-proline incorporation into nascent secreted collagen. $^3$H-labeled collagen is visualized by SDS-PAGE followed by autoradiography (Unemori and Amento, *J. Biol. Chem.* 265: 10681–10685, 1990). Glycosaminoglycan (GAG) secretion from dermal fibroblasts and chondrocytes is measured using a 1,9-dimethylmethylene blue dye binding assay (Farndale et al., *Biochim. Biophys. Acta* 883:173–177, 1986). Inhibition of cytokine activity is assayed by including zlmda33 with one or more cytokines known to be active in a given assay. Collagen and GAG assays, for example, are carried out in the presence of IL-1β or TGF-β to examine the ability of zlmda33 protein to modify the established responses to these cytokines.

Monocyte activation assays are carried out (1) to look for the ability of zlmda33 proteins to modulate monocyte activation, including attachment-induced or endotoxin-induced monocyte activation (Fuhlbrigge et al., *J. Immunol.* 138: 3799–3802, 1987). IL-1β and TNFα levels produced in response to activation are measured by ELISA (Biosource, Inc. Camarillo, Calif.). Monocyte/macrophage cells, by virtue of CD14 (LPS receptor), are exquisitely sensitive to endotoxin, and proteins with moderate levels of endotoxin-like activity will activate these cells.

In vitro assays for pro- and anti-inflammatory activity are known in the art. Exemplary activity assays include mitogenesis assays in which IL-1 responsive cells (e.g., the D10.N4.M murine T cell line) are incubated in the presence of IL-1 or a test protein for 72 hours at 37° C. in a 5% $CO_2$ atmosphere. IL-2 (and optionally IL-4) is added to the culture medium to enhance sensitivity and specificity of the assay. $^3$H-thymidine is then added, and incubation is continued for six hours. The amount of label incorporated is indicative of agonist activity. See, Hopkins and Humphreys, *J. Immunol. Methods* 120:271–276, 1989; Greenfeder et al., *J. Biol. Chem.* 270:22460–22466, 1995. Stimulation of cell proliferation can also be measured using thymocytes cultured in a test protein in combination with phytohemagglutinin. IL-1 is used as a control. Proliferation is detected as $^3$H-thymidine incorporation or metabolic breakdown of (MTT) (Mosman, ibid.).

Hematopoietic activity of zlmda33 proteins can be assayed on various hematopoietic cells in culture. Such assays include primary bone marrow colony assays and later stage lineage-restricted colony assays, which are known in the art (e.g., Holly et al., WIPO Publication WO 95/21920). Marrow cells plated on a suitable semi-solid medium (e.g., 50% methylcellulose containing 15% fetal bovine serum, 10% bovine serum albumin, and 0.6% PSN antibiotic mix) are incubated in the presence of test polypeptide, then examined microscopically for colony formation. Known hematopoietic factors are used as controls. Mitogenic activity of zlmda33 polypeptides on hematopoietic cell lines can be measured as disclosed above.

Cell migration is assayed essentially as disclosed by K ähler et al. (*Arteriosclerosis, Thrombosis, and Vascular Biology* 17:932–939, 1997). A protein is considered to be chemotactic if it induces migration of cells from an area of low protein concentration to an area of high protein concentration. A typical assay is performed using modified Boyden chambers with a polystryrene membrane separating the two chambers (Transwell®; Corning Costar® Corp.). The test sample, diluted in medium containing 1% BSA, is added to the lower chamber of a 24-well plate containing Transwells. Cells are then placed on the Transwell insert that has been pretreated with 0.2% gelatin. Cell migration is measured after 4 hours of incubation at 37° C. Non-migrating cells are wiped off the top of the Transwell membrane, and cells attached to the lower face of the membrane are fixed and stained with 0.1% crystal violet. Stained cells are then extracted with 10% acetic acid and absorbance is measured at 600 nm. Migration is then calculated from a standard calibration curve. Cell migration can also be measured using the matrigel method of Grant et al. ("Angiogenesis as a component of epithelial-mesenchymal interactions" in Goldberg and Rosen, *Epithelial-Mesenchymal Interaction in Cancer*, Birkhäuser Verlag, 1995, 235–248; Baatout, *Anticancer Research* 17:451–456, 1997).

Cell adhesion activity is assayed essentially as disclosed by LaFleur et al. (*J. Biol. Chem.* 272:32798–32803, 1997). Briefly, microtiter plates are coated with the test protein, non-specific sites are blocked with BSA, and cells (such as smooth muscle cells, leukocytes, or endothelial cells) are plated at a density of approximately $10^4$–$10^5$ cells/well. The wells are incubated at 37° C. (typically for about 60 minutes), then non-adherent cells are removed by gentle washing. Adhered cells are quantitated by conventional methods (e.g., by staining with crystal violet, lysing the cells, and determining the optical density of the lysate). Control wells are coated with a known adhesive protein, such as fibronectin or vitronectin.

Other metabolic effects of zlmda33 proteins can be measured by culturing target cells in the presence and absence of a protein and observing changes in adipogenesis, gluconeogenesis, glycogenolysis, lipogenesis, glucose uptake, or the like. Suitable assays are known in the art.

Proteins can be assayed for the ability to modulate axon guidance and growth. Suitable assays that detect changes in neuron growth patterns include, for example, those disclosed in Hastings, WIPO Publication WO 97/29189 and Walter et al., *Development* 101:685–696, 1987. Assays to measure the effects on neuron growth are well known in the art. For example, the C assay (e.g., Raper and Kapfhammer, *Neuron* 4:21–29, 1990 and Luo et al., *Cell* 75:217–227, 1993) can be used to determine collapsing activity of a protein of interest on growing neurons. Other methods that can assess protein-induced inhibition of neurite extension or divert such extension are also known. See, Goodman, *Annu. Rev. Neurosci.* 19:341–377, 1996. Conditioned media from cells expressing a protein of interest, or aggregates of such cells, can by placed in a gel matrix near suitable neural cells, such as dorsal root ganglia (DRG) or sympathetic ganglia explants, which have been co-cultured with nerve growth factor. Compared to control cells, protein-induced changes in neuron growth can be measured (as disclosed by, for example, Messersmith et al., *Neuron* 14:949–959, 1995 and Puschel et al., *Neuron* 14:941–948, 1995). Neurite outgrowth can be measured using neuronal cell suspensions grown in the presence of molecules of the present invention. See, for example, O'Shea et al., *Neuron* 7:231–237, 1991 and DeFreitas et al., *Neuron* 15:333–343, 1995.

Assays for angiogenic activity are also known in the art. For example, the effect of a protein of interest on primordial endothelial cells in angiogenesis can be assayed in the chick chorioallantoic membrane angiogenesis assay (Leung, *Science* 246:1306–1309, 1989; Ferrara, *Ann. NY Acad. Sci.* 752:246–256, 1995). Briefly, a small window is cut into the shell of an eight-day old fertilized egg, and a test substance is applied to the chorioallantoic membrane. After 72 hours, the membrane is examined for neovascularization. Other suitable assays include microinjection of early stage quail (*Coturnix coturnix japonica*) embryos as disclosed by Drake et al. (*Proc. Natl. Acad. Sci. USA* 92:7657–7661, 1995); the rodent model of corneal neovascularization disclosed by Muthukkaruppan and Auerbach (*Science* 205:1416–1418, 1979), wherein a test substance is inserted into a pocket in the cornea of an inbred mouse; and the hampster cheek pouch assay (Höckel et al., *Arch. Surg.* 128:423–429, 1993). Induction of vascular permeability, which is indicative of angiogenic activity, is measured in assays designed to detect leakage of protein from the vasculature of a test animal (e.g., mouse or guinea pig) after administration of a test compound (Miles and Miles, *J. Physiol.* 118:228–257, 1952; Feng et al., *J. Exp. Med.* 183:1981–1986, 1996). In vitro assays for angiogenic activity include the tridimensional collagen gel matrix model (Pepper et al. *Biochem. Biophys. Res. Comm.* 189:824–831, 1992 and Ferrara et al., *Ann. NY Acad. Sci.* 732:246–256, 1995), which measures the formation of tube-like structures by microvascular endothelial cells; and matrigel models (Grant et al., "Angiogenesis as a component of epithelial-mesenchymal interactions" in Goldberg and Rosen, *Epithelial-Mesenchymal Interaction in Cancer*, Birkhäuser Verlag, 1995, 235–248; Baatout, *Anticancer Research* 17:451–456, 1997), which are used to determine effects on cell migration and tube formation by endothelial cells seeded in matrigel, a basement membrane extract enriched in laminin. It is preferred to carry out angiogenesis assays in the presence and absence of vascular endothelial growth factor (VEGF) to assess possible combinatorial effects. It is also preferred to use VEGF as a control within in vivo assays.

Receptor binding can be measured by the competition binding method of Labriola-Tompkins et al., *Proc. Natl. Acad. Sci. USA* 88:11182–11186, 1991. In an exemplary assay for IL-1 receptor binding, membranes pepared from EL-4 thymoma cells (Paganelli et al., *J. Immunol.* 138:2249–2253, 1987) are incubated in the presence of the test protein for 30 minutes at 37° C. Labeled IL-1α or IL-1β is then added and the incubation is continued for 60 minutes. The assay is terminated by membrane filtration. The amount of bound label is determined by conventional means (e.g., γ counter). In an alternative assay, the ability of a test protein to compete with labeled IL-1 for binding to cultured human dermal fibroblasts is measured according to the method of Dower et al. (*Nature* 324:266–268, 1986). Briefly, cells are incubated in a round-bottomed, 96-well plate in a suitable culture medium (e.g., RPMI 1640 containing 1% BSA, 0.1% Na azide, and 20 mM HEPES pH 7.4) at 8° C. on a rocker platform in the presence of labeled IL-1. Various concentrations of test protein are added. After the incubation (typically about two hours), cells are separated from unbound label by centrifuging 60-$\mu$l aliquots through 200 $\mu$l of phthalate oils in 400-$\mu$l polyethylene centrifuge tubes and excising the tips of the tubes with a razor blade as disclosed by Segal and Hurwitz, *J. Immunol.* 118:1338–1347, 1977. Receptor binding assays for other cell types are known in the art. See, for example, Bowen-Pope and Ross, *Methods Enzymol.* 109:69–100, 1985.

Receptor binding can also be measured using immobilized receptors or ligand-binding receptor fragments. For example, an immobilized receptor can be exposed to its labeled ligand and unlabeled test protein, whereby a reduction in labeled ligand binding compared to a control is indicative of receptor-binding activity in the test protein. Within another format, a receptor or ligand-binding receptor fragment is immobilized on a biosensor (e.g., BIACore™, Pharmacia Biosensor, Piscataway, N.J.) and binding is determined. Antagonists of the native ligand will exhibit receptor binding but will exhibit essentially no activity in appropriate activity assays or will reduce the ligand-mediated response when combined with the native ligand. In view of the low level of receptor occupancy required to produce a response to some ligands (e.g., IL-1), a large excess of antagonist (typically a 10- to 1000-fold molar excess) may be necessary to neutralize ligand activity.

Receptor activation can be detected in target cells by: (1) measurement of adenylate cyclase activity (Salomon et al., *Anal. Biochem.* 58:541–48, 1974; Alvarez and Daniels, *Anal. Biochem.* 187:98–103, 1990); (2) measurement of change in intracellular cAMP levels using conventional radioimmunoassay methods (Steiner et al., *J. Biol. Chem.* 247:1106–13, 1972; Harper and Brooker, *J. Cyc. Nucl. Res.* 1:207–18, 1975); or (3) through use of a cAMP scintillation proximity assay (SPA) method (such as available from Amersham Corp., Arlington Heights, Ill.).

Proteins can be tested for serine protease activity or proteinase inhibitory activity using conventional assays. Substrate cleavage is conveniently assayed using a tetrapeptide that mimics the cleavage site of the natural substrate and which is linked, via a peptide bond, to a carboxyl-terminal para-nitro-anilide (pNA) group. The protease hydrolyzes the bond between the fourth amino acid residue and the pNA group, causing the pNA group to undergo a dramatic increase in absorbance at 405 nm. Suitable substrates can be synthesized according to known methods or obtained from commercial suppliers. Inhibitory activity is measured by adding a test sample to a reaction mixture containing enzyme and substrate, and comparing the observed enzyme activity to a control (without the test sample). A variety of such assays are known in the art, including assays measuring inhibition of trypsin, chymotrypsin, plasmin, cathepsin G, and human leukocyte elastase. See, for example, Petersen et al., *Eur. J. Biochem.* 235:310–316, 1996. In a typical procedure, the inhibitory activity of a test compound is measured by incubating the test compound with the proteinase, then adding an appropriate substrate, typically a chromogenic peptide substrate. See, for example, Norris et al. (*Biol. Chem. Hoppe-Seyler* 371:37–42, 1990). Various concentrations of the inhibitor are incubated in the presence of trypsin, plasmin, and plasma kallikrein in a low-salt buffer at pH 7.4, 25° C. After 30 minutes, the residual enzymatic activity is measured by the addition of a chromogenic substrate (e.g., S2251 (D-Val-Leu-Lys-Nan) or S2302

(D-Pro-Phe-Arg-Nan), available from Kabi, Stockholm, Sweden) and a 30-minute incubation. Inhibition of enzyme activity is indicated by a decrease in absorbance at 405 nm or fluorescence Em at 460 nm. From the results, the apparent inhibition constant $K_i$ is calculated. When a serine protease is prepared as an active precursor, it is activated by cleavage with a suitable protease (e.g., furin (Steiner et al., *J. Biol. Chem.* 267:23435–23438, 1992)) prior to assay. Assays of this type are well known in the art. See, for example, Lottenberg et al., *Thrombosis Research* 28:313–332, 1982; Cho et al., *Biochem.* 23:644–650, 1984; Foster et al., *Biochem.* 26:7003–7011, 1987). The inhibition of coagulation factors (e.g., factor VIIa, factor Xa) can be measured using chromogenic substrates or in conventional coagulation assays (e.g., clotting time of normal human plasma; Dennis et al., *J. Biol. Chem.* 270:25411–25417, 1995).

Blood coagulation and chromogenic assays, which can be used to detect both procoagulant, anticoagulant, and thrombolytic activities, are known in the art. For example, pro- and anticoagulant activities can be measured in a one-stage clotting assay using platelet-poor or factor-deficient plasma (Levy and Edgington, *J. Exp. Med.* 151:1232–1243, 1980; Schwartz et al., *J. Clin. Invest.* 67:1650–1658, 1981). As disclosed by Anderson et al. (*Proc. Natl. Acad. Sci. USA* 96:11189–11193, 1999), the effect of a test compound on platelet activation can be determined by a change in turbidity, and the procoagulant activity of activated platelets can be determined in a phospholipid-dependent coagulation assay. Activation of thrombin can be determined by hydrolysis of peptide p-nitroanilide substrates as disclosed by Lottenberg et al. (*Thrombosis Res.* 28:313–332, 1982). Other procoagulant, anticoagulant, and thrombolytic activities can be measured using appropriate chromogenic substrates, a variety of which are available from commercial suppliers. See, for example, Kettner and Shaw, *Methods Enzymol.* 80:826–842, 1981.

Anti-microbial activity of proteins is evaluated by techniques that are known in the art. For example, anti-microbial activity can be assayed by evaluating the sensitivity of microbial cell cultures to test agents and by evaluating the protective effect of test agents on infected mice. See, for example, Musiek et al., *Antimicrob. Agents Chemothr.* 3:40, 1973. Antiviral activity can also be assessed by protection of mammalian cell cultures. Known techniques for evaluating anti-microbial activity include, for example, Barsum et al., *Eur. Respir. J.* 8:709–714, 1995; Sandovsky-Losica et al., *J. Med. Vet. Mycol (England)* 28:279–287, 1990; Mehentee et al., *J. Gen. Microbiol (England)* 135(:2181–2188, 1989; and Segal and Savage, *J. Med. Vet. Mycol.* 24:477–479, 1986. Assays specific for anti-viral activity include, for example, those described by Daher et al., *J. Virol.* 60:1068–1074, 1986.

The assays disclosed above can be modified by those skilled in the art to detect the presence of agonists and antagonists of a selected protein of interest.

Expression of zlmda33 polynucleotides in animals provides models for further study of the biological effects of overproduction or inhibition of protein activity in vivo. Zlmda33-encoding polynucleotides and antisense polynucleotides can be introduced into test animals, such as mice, using viral vectors or naked DNA, or transgenic animals can be produced.

One in vivo approach for assaying proteins of the present invention utilizes viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161–89, 1994; and Douglas and Curiel, *Science & Medicine* 4:44–53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene is deleted from the viral vector, and the virus will not replicate unless the E1 gene is provided by the host cell (e.g., the human 293 cell line). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein. Secreted proteins will enter the circulation in the highly vascularized liver, and effects on the infected animal can be determined.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., *J. Biol. Chem.* 263:14621–14624, 1988; Wu et al., *J. Biol. Chem.* 267:963–967, 1992; and Johnston and Tang, *Meth. Cell Biol.* 43:353–365, 1994.

Transgenic mice, engineered to express a zlmda33 gene, and mice that exhibit a complete absence of zlmda33 gene function, referred to as "knockout mice" (Snouwaert et al., *Science* 257:1083, 1992), can also be generated (Lowell et al., *Nature* 366:740–742, 1993). These mice can be employed to study the zlmda33 gene and the protein encoded thereby in an in vivo system. Transgenic mice are particularly useful for investigating the role of zlmda33 proteins in early development in that they allow the identification of developmental abnormalities or blocks resulting from the over- or underexpression of a specific factor. See also, Maisonpierre et al., *Science* 277:55–60, 1997 and Hanahan, *Science* 277:48–50, 1997. Promoters for transgenic expression include promoters from metallothionein and albumin genes.

Inhibitory polynucleotides can be used to inhibit zlmda33 gene expression as disclosed in more detail below to examine the effects of such inhibition in vivo. Inhibitory polynucleotides can also be used to inhibit expression of zlmda33 polypeptide-encoding genes in cell culture.

Biological activities of test proteins can also be measured in animal models by administering the test protein, by itself or in combination with other agents, including other proteins. Using such models facilitates the assay of the test protein by itself or as an inhibitor or modulator of another agent, and also facilitates the measurement of combinatorial effects of bioactive compounds.

Anti-inflammatory activity can be tested in animal models of inflammatory disease. For example, animal models of psoriasis include the analysis of histological alterations in adult mouse tail epidermis (Hofbauer et al, *Brit. J. Dermatol.* 118:85–89, 1988; Bladon et al., *Arch Dermatol. Res.* 277:121–125, 1985). In this model, anti-psoriatic activity is indicated by the induction of a granular layer and orthokeratosis in areas of scale between the hinges of the tail epidermis. Typically, a topical ointment comprising a test compound is applied daily for seven consecutive days, then the animal is sacrificed, and tail skin is examined histologically. An additional model is provided by grafting psoriatic human skin to congenitally athymic (nude) mice (Krueger et al., *J. Invest. Dermatol.* 64:307–312, 1975). Such grafts have been shown to retain the characteristic histology for up to eleven weeks. As in the mouse tail model, the test composition is applied to the skin at predetermined intervals for a period of one to several weeks, at which time the animals are sacrificed and the skin grafts examined histologically. A third model has been disclosed by Fretland et al. (*Inflammation* 14:727–739, 1990). Briefly, inflammation is induced in guinea pig epidermis by topically applying phorbol ester (phorbol-12-myristate-13-acetate; PMA), typically at ca. 2 g/ml in acetone, to one ear and vehicle to the contralateral ear. Test compounds are applied concurrently with the PMA, or may be given orally. Histological analysis is performed at 96 hours after application of PMA. This model duplicates many symptoms of human psoriasis, including edema, inflammatory cell diapedesis and infiltration, high $LTB_4$ levels and epidermal proliferation.

Cerebral ischemia can be studied in a rat model as disclosed by Relton et al. (ibid.) and Loddick et al. (ibid.).

The effect of a test protein on primordial endothelial cells in angiogenesis can be assayed in the chick chorioallantoic membrane angiogenesis assay (Leung, *Science* 246:1306–1309, 1989; Ferrara, *Ann. NY Acad. Sci.* 752:246–256, 1995). Briefly, a small window is cut into the shell of an eight-day old fertilized egg, and a test substance is applied to the chorioallantoic membrane. After 72 hours, the membrane is examined for neovascularization. Embryo microinjection of early stage quail (*Coturnix coturnix japonica*) embryos can also be used (Drake et al., *Proc. Natl. Acad. Sci. USA* 92:7657–7661, 1995). Briefly, a solution containing the protein is injected into the interstitial space between the endoderm and the splanchnic mesoderm of early-stage embryos using a micropipette and micromanipulator system. After injection, embryos are placed ventral side down on a nutrient agar medium and incubated for 7 hours at 37° C. in a humidified $CO_2$/air mixture (10%/90%). Vascular development is assessed by microscopy of fixed, whole-mounted embryos and sections.

Stimulation of coronary collateral growth can be measured in known animal models, including a rabbit model of peripheral limb ischemia and hind limb ischemia and a pig model of chronic myocardial ischemia (Ferrara et al., *Endocrine Reviews* 18:4–25, 1997). Test proteins are assayed in the presence and absence of VEGF and basic FGF to test for combinatorial effects. These models can be modified by the use of adenovirus or naked DNA for gene delivery as disclosed in more detail above, resulting in local expression of the test protein(s).

Angiogenic activity can also be tested in a rodent model of corneal neovascularization as disclosed by Muthukkaruppan and Auerbach, *Science* 205:1416–1418, 1979, wherein a test substance is inserted into a pocket in the cornea of an inbred mouse. For use in this assay, proteins are combined with a solid or semi-solid, biocompatible carrier, such as a polymer pellet. Angiogenesis is followed microscopically. Vascular growth into the corneal stroma can be detected in about 10 days.

Angiogenic activity can also be tested in the hampster cheek pouch assay (Höckel et al., *Arch. Surg.* 128:423–429, 1993). A test substance is injected subcutaneiously into the cheek pouch, and after five days the pouch is examined under low magnification to determine the extent of neovascularization. Tissue sections can also be examined histologically.

Induction of vascular permeability is measured in assays designed to detect leakage of protein from the vasculature of a test animal (e.g., mouse or guinea pig) after administration of a test compound (Miles and Miles, *J. Physiol.* 118:228–257, 1952; Feng et al., *J. Exp. Med.* 183:1981–1986, 1996).

Wound-healing models include the linear skin incision model of Mustoe et al. (*Science* 237:1333, 1987). In a typical procedure, a 6-cm incision is made in the dorsal pelt of an adult rat, then closed with wound clips. Test substances and controls (in solution, gel, or powder form) are applied before primary closure. It is preferred to limit administration to a single application, although additional applications can be made on succeeding days by careful injection at several sites under the incision. Wound breaking strength is evaluated between 3 and 21 days post wounding. In a second model, multiple, small, full-thickness excisions are made on the ear of a rabbit. The cartilage in the ear splints the wound, removing the variable of wound contraction from the evaluation of closure. Experimental treatments and controls are applied. The geometry and anatomy of the wound site allow for reliable quantification of cell ingrowth and epithelial migration, as well as quantitative analysis of the biochemistry of the wounds (e.g., collagen content). See, Mustoe et al., *J. Clin. Invest.* 87:694, 1991. The rabbit ear model can be modified to create an ischemic wound environment, which more closely resembles the clinical situation (Ahn et al., *Ann. Plast. Surg.* 24:17, 1990). Within a third model, healing of partial-thickness skin wounds in pigs or guinea pigs is evaluated (LeGrand et al., *Growth Factors* 8:307, 1993). Experimental treatments are applied daily on or under dressings. Seven days after wounding, granulation tissue thickness is determined. This model is preferred for dose-response studies, as it is more quantitative than other in vivo models of wound healing. A full thickness excision model can also be employed. Within this model, the epidermis and dermis are removed down to the panniculus carnosum in rodents or the subcutaneous fat in pigs. Experimental treatments are applied topically on or under a dressing, and can be applied daily if desired. The wound closes by a combination of contraction and cell ingrowth and proliferation. Measurable endpoints include time to wound closure, histologic score, and biochemical parameters of wound tissue. Impaired wound healing models are also known in the art (e.g., Cromack et al., *Surgery* 113:36, 1993; Pierce et al., *Proc. Natl. Acad. Sci. USA* 86:2229, 1989; Greenhalgh et al., *Amer. J. Pathol.* 136:1235, 1990). Delay or prolongation of the wound healing process can be induced pharmacologically by treatment with steroids, irradiation of the wound site, or by concomitant disease states (e.g., diabetes). Linear incisions or full-thickness excisions are most commonly used as the experimental wound. Endpoints are as disclosed above for each type of wound. Subcutaneous implants can be used to assess compounds acting in the early stages of wound healing (Broadley et al., *Lab. Invest.* 61:571, 1985; Sprugel et al., *Amer. J. Pathol.* 129: 601, 1987). Implants are prepared in a porous, relatively noninflammatory container (e.g., polyethylene sponges or expanded polytetrafluoroethylene implants filled with bovine collagen) and placed subcutaneously in mice or rats. The interior of the implant is empty of cells, producing a "wound space" that is well-defined and separable from the preexisting tissue. This arrangement allows the assessment of cell influx and cell type as well as the measurement of vasculogenesis/angiogenesis and extracellular matrix production.

Inhibition of tumor metastasis can be assessed in mice into which cancerous cells or tumor tissue have been introduced by implantation or injection (e.g., Brown, *Advan. Enzyme Regul.* 35:293–301, 1995; Conway et al., *Clin. Exp. Metastasis* 14:115–124, 1996).

Effects on fibrinolysis can be measured in a rat model wherein the enzyme batroxobin and radiolabeled fibrinogen are administered to test animals. Inhibition of fibrinogen activation by a test compound is seen as a reduction in the circulating level of the label as compared to animals not receiving the test compound. See, Lenfors and Gustafsson, *Semin. Thromb. Hemost.* 22:335–342, 1996.

The polypeptides, nucleic acids and antibodies of the present invention may be used in diagnosis or treatment of disorders associated with cell loss or abnormal cell physiology (including cancer). Analysis of gene expression has shown that zlmda33 is expressed in ovarian and uterine tumors, but not in the corresponding normal tissues. Zlmda33 is thus a diagnostic marker of these tumors. Those skilled in the art will recognize that assays can be performed on body fluids (e.g., plasma, serum, urine), tissue samples, or isolated cells. Such diagnosis will generally be carried out by testing a fluid or tissue sample using conventional immunoassay methods such as enzyme-linked immunoadsorption assays or radioimmune assays. Assays of these types are well known in the art. See, for example, Hart et al., *Biochem.* 29:166–172, 1990; Ma et al., *British J. Haematol.* 80:431–436, 1992; and Andre et al., *Clin. Chem.* 38/5:758–763, 1992. In addition, zlmda33 provides a target for therapeutic agents.

Assays for zlmda33 can be used to detect soluble protein in body fluids (e.g., plasma, serum, urine) or cell-associated protein in isolated cells, cell fractions (e.g., membranes), or tissue samples. General methods for collecting samples and assaying for the presence and amount of a protein are known in the art. Assays will commonly employ an anti-zlmda33 antibody or other specific binding partner (e.g., soluble receptor). The antibody or binding partner can itself be labeled, thereby directly providing a detectable signal, or a labeled second antibody or binding partner can be used to provide the signal.

Labeled anti-zlmda33 antibodies or other binding partners may be used in vivo for imaging tumors or other sites of abnormal cell proliferation. Anti-zlmda33 antibodies or other binding partners can be directly or indirectly conjugated to radionuclides or other detectable molecules, and these conjugates used for diagnostic or therapeutic applications. For in vivo use, an anti-zlmda33 antibody or other binding partner can be directly or indirectly coupled to a detectable molecule and delivered to a mammal having cells, tissues, or organs that express zlmda33. Suitable detectable molecules include radionuclides, enzymes, substrates, cofactors, inhibitors, fluorescent markers, chemiluminescent markers, magnetic particles, electron-dense compounds, heavy metals, and the like. These can be either directly attached to the antibody or other binding partner, or indirectly attached according to known methods, such as through a chelating moiety. For indirect attachment of a detectable molecule, the detectable molecule can be conjugated with a first member of a complementary/anticomplementary pair, wherein the second member of the pair is bound to the anti-zlmda33 antibody or other binding partner. Biotin/streptavidin is an exemplary complementary/anticomplementary pair; others will be evident to those skilled in the art. The labeled compounds described herein can be delivered intravenously, intra-arterially or intraductally, or may be introduced locally at the intended site of action.

As used herein, the term "antibodies" includes polyclonal antibodies, monoclonal antibodies, antigen-binding fragments thereof such as F(ab')$_2$ and Fab fragments, single chain antibodies, and the like, including genetically engineered antibodies. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains. Antibodies are defined to be specifically binding if they bind to a zlmda33 polypeptide or protein with an affinity at least 10-fold greater than the binding affinity to control (non-zlmda33) polypeptide or protein. The affinity of a monoclonal antibody can be readily determined by one of ordinary skill in the art (see, for example, Scatchard, *Ann. NY Acad. Sci.* 51: 660–672, 1949).

Methods for preparing polyclonal and monoclonal antibodies are well known in the art (see for example, Hurrell, J. G. R., Ed., *Monoclonal Hybridoma Antibodies: Techniques and Applications*, CRC Press, Inc., Boca Raton, Fla., 1982). As would be evident to one of ordinary skill in the art, polyclonal antibodies can be generated from a variety of warm-blooded animals such as horses, cows, goats, sheep, dogs, chickens, rabbits, mice, and rats. The immunogenicity of a zlmda33 polypeptide may be increased through the use of an adjuvant such as alum (aluminum hydroxide) or Freund's complete or incomplete adjuvant. Polypeptides useful for immunization also include fusion polypeptides, such as fusions of a zlmda33 polypeptide or a portion thereof with an immunoglobulin polypeptide or with maltose binding protein. If the polypeptide is "hapten-like", it may be advantageously joined or linked to a macromolecular carrier (such as keyhole limpet hemocyanin (KLH), bovine serum albumin (BSA) or tetanus toxoid) for immunization.

Alternative techniques for generating or selecting antibodies include in vitro exposure of lymphocytes to zlmda33 polypeptides, and selection of antibody display libraries in phage or similar vectors (e.g., through the use of immobilized or labeled zlmda33 polypeptide). Human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

A variety of assays known to those skilled in the art can be utilized to detect antibodies that specifically bind to zlmda33 polypeptides. Exemplary assays are described in detail in *Antibodies: A Laboratory Manual*, Harlow and Lane (Eds.), Cold Spring Harbor Laboratory Press, 1988. Representative examples of such assays include concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

In addition to the diagnostic and therapeutic uses disclosed above, anti-zlmda33 antibodies can be used for affinity purification of the protein, for immunolocalization within whole animals or tissue sections, for immunohistochemistry, and as antagonists to block protein activity in vitro and in vivo. Antibodies to zlmda33 can also be used in analytical methods employing fluorescence-activated cell sorting (FACS), for screening expression libraries, and for generating anti-idiotypic antibodies.

For pharmaceutical use, zlmda33 proteins, anti-zlmda33 antibodies, and other bioactive compounds are formulated for topical or parenteral, particularly intravenous or subcutaneous, delivery according to conventional methods. In general, pharmaceutical formulations will include a zlmda33 polypeptide, antibody, or other compound in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in *Remington: The Science and Practice of Pharmacy*, Gennaro, ed., Mack Publishing Co., Easton, Pa., 19th ed., 1995. Zlmda33 will commonly be used in a concentration of about 10 to 100 $\mu$g/ml of total volume, although concentrations in the range of 1 ng/ml to 1000 $\mu$g/ml may be used. For topical application the protein will be applied in the range of 0.1–10 $\mu$g/cm$^2$ of surface area. The exact dose will be determined by the clinician according to accepted standards, taking into account the nature and severity of the condition to be treated, patient traits, etc. Determination of dose is within the level of ordinary skill in the art. Dosing is daily or intermittently over the period of treatment. Intravenous administration will be by bolus injection or infusion over a typical period of one to several hours. Sustained release formulations can also be employed.

Within the laboratory research field, zlmda33 proteins can also be used as molecular weight standards or as reagents in assays for determining circulating levels of the protein, such as in the diagnosis of disorders characterized by over- or under-production of zlmda33 protein or in the analysis of cell phenotype.

Polynucleotides and polypeptides of the present invention will additionally find use as educational tools within laboratory practicum kits for courses related to genetics, molecular biology, protein chemistry, and antibody production and analysis. Due to their unique polynucleotide and polypeptide sequences, molecules of zlmda33 can be used as standards or as "unknowns" for testing purposes. For example, zlmda33 polynucleotides can be used as an aid in teaching a student how to prepare expression constructs for bacterial, viral, and/or mammalian expression, including fusion constructs, wherein zlmda33 is the gene to be expressed; for experimentally determining the restriction endonuclease cleavage sites of the polynucleotides (which can be determined from the sequence using conventional computer software, such as MapDraw™ (DNASTAR, Madison, Wis.)); determining mRNA and DNA localization of zlmda33 polynucleotides in tissues (e.g., by Northern blotting, Southern blotting, or polymerase chain reaction); and for identifying related polynucleotides and polypeptides by nucleic acid hybridization.

Zlmda33 polypeptides can be used educationally as aids to teach preparation of antibodies; identification of proteins by Western blotting; protein purification; determination of the weight of expressed zlmda33 polypeptides as a ratio to total protein expressed; identification of peptide cleavage sites; coupling amino and carboxyl terminal tags; amino acid sequence analysis; as well as, but not limited to, monitoring biological activities of both the native and tagged protein (i.e., receptor binding, signal transduction, proliferation, and differentiation) in vitro and in vivo. Zlmda33 polypeptides can also be used to teach analytical skills such as mass spectrometry, circular dichroism to determine conformation, x-ray crystallography to determine the three-dimensional structure in atomic detail, nuclear magnetic resonance spectroscopy to reveal the structure of proteins in solution, and the like. For example, a kit containing a zlmda33 polypeptide can be given to the student to analyze. Since the amino acid sequence would be known by the instructor, the polypeptide can be given to the student as a test to determine the skills or develop the skills of the student, and the instructor would then know whether or not the student has correctly analyzed the polypeptide. Since every polypeptide is unique, the educational utility of zlmda33 would be unique unto itself.

Zlmda33 proteins can also be used to identify inhibitors of their activity. Test compounds are added to the assays disclosed above to identify compounds that inhibit the activity of zlmda33 protein. In addition to those assays disclosed above, cellular proteins that bind to and interact with zlmda33 can be identified by, for example, screening cDNA libraries in a yeast two-hybrid system (Fields and Song, *Nature* 340:245–246, 1989; Gyuris et. al., *Cell* 75:791–803, 1993; and Li and Fields, *FASEB J.* 7:957–963, 1993). Briefly, the yeast two-hybrid system allows the detection of protein-protein interactions through the use of transcriptional activators, which are modular in nature. A known gene is cloned into a "bait" vector, from which it is expressed as a fusion protein the binding domain of a transcriptional activator. The cDNA library is cloned into a second ("prey") vector for expression of fusion proteins comprising the activation domain of the transcriptional activator. When proteins expressed from the two vectors interact, a functional transcriptional activator is produced, allowing expression of a selectable marker and consequent growth of the host cell. Vectors and other reagents for yeast two-hybrid systems are available from commercial suppliers (e.g., Clontech Laboratories, Inc., Palo Alto, Calif. and Invitrogen, Carlsbad, Calif.). Proteins that bind to zlmda33 provide additional targets through which zlmda activity can be modulated.

The polynucleotides of the present invention can be used in diagnostic applications. For example, the zlmda33 gene, a probe comprising zlmda33 DNA or RNA, or a subsequence thereof can be used to determine the presence of mutations at or near the zlmda33 locus. Detectable chromosomal aberrations at the zlmda33 gene locus include, but are not limited to, aneuploidy, gene copy number changes, insertions, deletions, restriction site changes, and rearrangements. These aberrations can occur within the coding sequence, within introns, or within flanking sequences, including upstream promoter and regulatory regions, and may be manifested as physical alterations within a coding sequence or changes in gene expression level. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targetted for analysis. For gross analysis of genes, a polynucleotide probe may comprise an entire exon or more. Probes will generally comprise a polynucleotide linked to a signal-generating moiety such as a radionucleotide. In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (c) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; A. J. Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–38, 1991).

Those skilled in the art will also recognize that the diagnostic techniques disclosed above can be applied to detect expression of zlmda33 (production of mRNA) within a cell or tissue, including a cell or tissue obtained from a patient. As disclosed above, a genetic sample is analyzed using probes or primers comprising zlmda33 DNA or RNA, or a subsequence thereof.

Sequence tagged sites (STSs) can also be used independently for chromosomal localization. An STS is a DNA sequence that is unique in the human genome and can be used as a reference point for a particular chromosome or region of a chromosome. An STS is defined by a pair of oligonucleotide primers that are used in a polymerase chain reaction to specifically detect this site in the presence of all other genomic sequences. Since STSs are based solely on DNA sequence they can be completely described within an electronic database, for example, Database of Sequence Tagged Sites (dbSTS), GenBank (National Center for Biological Information, National Institutes of Health, Bethesda, Md. http://www.ncbi.nlm.nih.gov), and can be searched with a gene sequence of interest for the mapping data contained within these short genomic landmark STS sequences.

The zlmda33 gene maps to human chromosome 8 at 8p23.-p22. A description of this region of the genome is available from the OMIM™ Database, Johns Hopkins University, 2000. The zlmda33 gene is located in a region of chromosome 8 that has been found to be deleted in many human epithelial malignancies, including liver cancer, and is involved in a translocation event associated with hepatitis B virus integration, an event that has been implicated in liver oncogenesis. It is believed that one or more tumor suppressor genes may be located in this region of chromosome 8. See, Pineau et al., *J. Virol.* 70:7280–7284, 1996.

Inhibitors of zlmda33 activity (zlmda33 antagonists) include anti-zlmda33 antibodies, inactive receptor-binding fragments of zlmda33 polypeptides, soluble zlmda33 receptors, and other peptidic and non-peptidic agents (including inhibitory polynucleotides and small molecule inhibitors). Such antagonists can be used to block the effects of zlmda33 on cells or tissues. Antagonists are formulated for pharmaceutical use as generally disclosed above, taking into account the precise chemical and physical nature of the inhibitor and the condition to be treated. The relevant determinations are within the level of ordinary skill in the formulation art.

Polynucleotides encoding zlmda33 polypeptides and inhibitory polynucleotides are useful within gene therapy applications where it is desired to increase or inhibit zlmda33 activity. If a mammal has a mutated or absent zlmda33 gene, a zlmda33 gene can be introduced into the cells of the mammal. In one embodiment, a gene encoding a zlmda33 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective *herpes simplex* virus 1 (HSV1) vector (Kaplitt et al., *Molec. Cell. Neurosci.* 2:320–330, 1991); an attenuated adenovirus vector, such as the vector described by Stratford-Perricaudet et al., *J. Clin. Invest.* 90:626–630, 1992; and a defective adeno-associated virus vector (Samulski et al., *J. Virol.* 61:3096–3101, 1987; Samulski et al., *J. Virol.* 63:3822–3888, 1989). Within another embodiment, a zlmda33 gene can be introduced in a retroviral vector as described, for example, by Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; Dougherty et al., WIPO Publication WO 95/07358; and Kuo et al., *Blood* 82:845, 1993. Alternatively, the vector can be introduced by liposome-mediated transfection ("lipofection"). Synthetic cationic lipids can be used to prepare liposomes for in vivo transfection (Felgner et al., *Proc. Natl. Acad. Sci. USA* 84:7413–7417, 1987; Mackey et al., *Proc. Natl. Acad. Sci. USA* 85:8027–8031, 1988). The use of lipofection to introduce exogenous polynucleotides into specific organs in vivo has certain practical advantages, including molecular targeting of liposomes to specific cells. Directing transfection to particular cell types is particularly advantageous in a tissue with cellular heterogeneity, such as the pancreas, liver, kidney, and brain. Lipids may be chemically coupled to other molecules for the purpose of targeting. Peptidic and non-peptidic molecules can be coupled to liposomes chemically. Within another embodiment, cells are removed from the body, a vector is introduced into the cells as a naked DNA plasmid, and the transformed cells are re-implanted into the body as disclosed above.

Inhibitory polynucleotides can be used to inhibit expression of zlmda33. Inhibitory polynucleotides include antisense polynucleotides, ribozymes, and external guide sequences.

Antisense polynucleotides can be used to inhibit zlmda33 gene transcription. Polynucleotides that are complementary to a segment of a zlmda33-encoding polynucleotide (e.g., a polynucleotide as set forth in SEQ ID NO:1) are designed to bind to zlmda33-encoding mRNA and to inhibit translation of such mRNA. Antisense polynucleotides can be targetted to specific tissues using a gene therapy approach with specific vectors and/or promoters, such as viral delivery systems.

Ribozymes can also be used as zlmda33 antagonists. Ribozymes are RNA molecules that contain a catalytic center and a target RNA binding portion. The term includes RNA enzymes, self-splicing RNAs, self-cleaving RNAs, and nucleic acid molecules that perform these catalytic functions. A ribozyme selectively binds to a target RNA molecule through complementary base pairing, bringing the catalytic center into close proximity with the target sequence. The ribozyme then cleaves the target RNA and is released, after which it is able to bind and cleave additional molecules. A nucleic acid molecule that encodes a ribozyme is termed a "ribozyme gene." Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). An expression vector can be constructed in which a regulatory element is operably linked to a nucleotide sequence that encodes a ribozyme.

In another approach, expression vectors can be constructed in which a regulatory element directs the production of RNA transcripts capable of promoting RNase P-mediated cleavage of mRNA molecules that encode a zlmda33 polypeptide. An external guide sequence is constructed for directing the endogenous ribozyme, RNase P, to a particular species of intracellular mRNA, which is subsequently cleaved by the cellular ribozyme (see, for example, Altman et al., U.S. Pat. No. 5,168,053; Yuan et al., *Science* 263:1269, 1994; Pace et al., WIPO Publication No. WO 96/18733; George et al., WIPO Publication No. WO 96/21731; and Werner et al., WIPO Publication No. WO 97/33991). An external guide sequence generally comprises a ten- to fifteen-nucleotide sequence complementary to zlmda33 mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

The invention is further illustrated by the following non-limiting examples.

EXAMPLES

Example 1

Recombinant zlmda33 is produced in *E. coli* using a $His_6$ tag/maltose binding protein (MBP) double affinity fusion system as generally disclosed by Pryor and Leiting, *Prot. Expr. Pur.* 10:309–319, 1997. A thrombin cleavage site is placed at the junction between the affinity tag and zlmda33 sequences.

The fusion construct is assembled in the vector pTAP98, which comprises sequences for replication and selection in *E. coli* and yeast, the *E. coli* tac promoter, and a unique SmaI site just downstream of the MBP-$His_6$-thrombin site coding sequences. The zlmda33 cDNA (SEQ ID NO:1) is amplified by PCR using primers each comprising 40 bp of sequence homologous to vector sequence and 25 bp of sequence that anneals to the cDNA. The reaction is run using Taq DNA polymerase (Boehringer Mannheim, Indianapolis, Ind.) for 30 cycles of 94° C., 30 seconds; 60° C., 60 seconds; and 72° C., 60 seconds. One microgram of the resulting fragment is mixed with 100 ng of SmaI-cut pTAP98, and the mixture is transformed into yeast to assemble the vector by homologous recombination (Oldenburg et al., *Nucl. Acids. Res.* 25:451–452, 1997). $Ura^+$ transformants are selected.

Plasmid DNA is prepared from yeast transformants and transformed into *E. coli* MC1061. Pooled plasmid DNA is then prepared from the MC1061 transformants by the miniprep method after scraping an entire plate. Plasmid DNA is analyzed by restriction digestion.

*E. coli* strain BL21 is used for expression of zlmda33. Cells are transformed by electroporation and grown on minimal glucose plates containing casamino acids and ampicillin.

Protein expression is analyzed by gel electrophoresis. Cells are grown in liquid glucose media containing casamino acids and ampicillin. After one hour at 37° C., IPTG is added to a final concentration of 1 mM, and the cells are grown for an additional 2–3 hours at 37° C. Cells are disrupted using glass beads, and extracts are prepared.

Example 2

Larger scale cultures of zlmda33 transformants are prepared by the method of Pryor and Leiting (ibid.). 100-mil cultures in minimal glucose media containing casamino acids and 100 µg/ml ampicillin are grown at 37° C. in 500-ml baffled flasks to $OD_{600}$≈0.5. Cells are harvested by centrifugation and resuspended in 100 ml of the same media at room temperature. After 15 minutes, IPTG is added to 0.5 mM, and cultures are incubated at room temperature (ca. 22.5° C.) for 16 to 20 hours with shaking at 125 rpm. The culture is harvested by centrifugation, and cell pellets are stored at −70° C.

Example 3

For larger-scale protein preparation, 500-mil cultures of *E. coli* BL21 expressing the zlmda33-MBP-$His_6$ fusion protein are prepared essentially as disclosed in Example 3. Cell pellets are resuspended in 100 ml of binding buffer (20 mM Tris, pH 7.58, 100 mM NaCl, 20 mM $NaH_2PO_4$, 0.4 mM 4-(2-Aminoethyl)-benzenesulfonyl fluoride hydrochloride [Pefabloc® SC; Boehringer-Mannheim, Indianapolis, Ind.], 2 µg/ml Leupeptin, 2 µg/ml Aprotinin). The cells are lysed in a French press at 30,000 psi, and the lysate is centrifuged at 18,000× g for 45 minutes at 4° C. to clarify it. Protein concentration is estimated by gel electrophoresis with a BSA standard.

Recombinant zlmda33 fusion protein is purified from the lysate by affinity chromatography. Immobilized cobalt resin (Talon® metal affinity resin; Clontech Laboratories, Inc., Palo Alto, Calif.) is equilibrated in binding buffer. One ml of packed resin per 50 mg protein is combined with the clarified supernatant in a tube, and the tube is capped and sealed, then placed on a rocker overnight at 4° C. The resin is then pelleted by centrifugation at 4° C. and washed three times with binding buffer. Protein is eluted with binding buffer containing 0.2M imidazole. The resin and elution buffer are mixed for at least one hour at 4° C., the resin is pelleted, and the supernatant is removed. An aliquot is analyzed by gel electrophoresis, and concentration is estimated. Amylose resin is equilibrated in amylose binding buffer (20 mM Tris-HCl, pH 7.0, 100 mM NaCl, 10 mM EDTA) and combined with the supernatant from the Talon resin at a ratio of 2 mg fusion protein per ml of resin. Binding and washing steps are carried out as disclosed above. Protein is eluted with amylose binding buffer containing 10 mM maltose using as small a volume as possible to minimize the need for subsequent concentration. The eluted protein is analyzed by gel electrophoresis and staining with Coomassie blue using a BSA standard, and by Western blotting using an anti-MBP antibody.

Example 4

An expression plasmid containing all or part of a polynucleotide encoding zlmda33 is constructed via homologous recombination. A fragment of zlmda33 cDNA is isolated by PCR using primers that comprise, from 5' to 3' end, 40 bp of flanking sequence from the vector and 17 bp corresponding to the amino and carboxyl termini from the open reading frame of zlmda33. The resulting PCR product includes flanking regions at the 5' and 3' ends corresponding to the vector sequences flanking the zlmda33 insertion point. Ten $\mu$l of the 100 $\mu$l PCR reaction mixture is run on a 0.8% low-melting-temperature agarose (SeaPlaque GTG®; FMC BioProducts, Rockland, Me.) gel with 1×TBE buffer for analysis. The remaining 90 $\mu$l of the reaction mixture is precipitated with the addition of 5 $\mu$l 1 M NaCl and 250 $\mu$l of absolute ethanol.

The plasmid pZMP6, which has been cut with SmaI, is used for recombination with the PCR fragment. Plamid pZMP6 is a mammalian expression vector containing an expression cassette having the cytomegalovirus immediate early promoter, multiple restriction sites for insertion of coding sequences, a stop codon, and a human growth hormone terminator; an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae. It was constructed from pZP9 (deposited at the American Type Culture Collection, 10801 University Boulevard, Manassas, Va. 20110–2209, under Accession No. 98668) with the yeast genetic elements taken from pRS316 (available from the American Type Culture Collection, 10801 University Boulevard, Manassas, Va. 20110–2209, under Accession No. 77145), an internal ribosome entry site (IRES) element from poliovirus, and a sequence encoding the extracellular domain of CD8 truncated at the C-terminal end of the transmembrane domain.

One hundred microliters of competent yeast (S. cerevisiae) cells are combined with 10 $\mu$l of the DNA preparations from above and transferred to a 0.2-cm electroporation cuvette. The yeast/DNA mixture is electropulsed using power supply (BioRad Laboratories, Hercules, Calif.) settings of 0.75 kV (5 kV/cm), ∞ ohms, 25 $\mu$F. To each cuvette is added 600 $\mu$l of 1.2 M sorbitol, and the yeast is plated in two 300-$\mu$l aliquots onto two URA-D (selective media lacking uracil and containing glucose) plates and incubated at 30° C. After about 48 hours, the Ura$^+$ yeast transformants from a single plate are resuspended in 1 ml H$_2$O and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA).

Five hundred microliters of the lysis mixture is added to an Eppendorf tube containing 300 $\mu$l acid-washed glass beads and 200 $\mu$l phenol-chloroform, vortexed for 1 minute intervals two or three times, and spun for 5 minutes in an Eppendorf centrifuge at maximum speed. Three hundred microliters of the aqueous phase is transferred to a fresh tube, and the DNA is precipitated with 600 $\mu$l ethanol (EtOH), followed by centrifugation for 10 minutes at 4° C. The DNA pellet is resuspended in 10 $\mu$l H$_2$O.

Transformation of electrocompetent E. coli host cells (Electromax DH10B™ cells; obtained from Life Technologies, Inc., Gaithersburg, Md.) is done with 0.5–2 ml yeast DNA prep and 40 $\mu$l of cells. The cells are electropulsed at 1.7 kV, 25 $\mu$F, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) is plated in 250-$\mu$l aliquots on four LB AMP plates (LB broth (Lennox), 1.8% Bacto™ Agar (Difco), 100 mg/L Ampicillin).

Individual clones harboring the correct expression construct for zlmda33 are identified by restriction digestion to verify the presence of the zlmda33 insert and to confirm that the various DNA sequences have been joined correctly to one another. The inserts of positive clones are subjected to sequence analysis. Larger scale plasmid DNA is isolated using a commercially available kit (QIAGEN Plasmid Maxi Kit, Qiagen, Valencia, Calif.) according to manufacturer's instructions. The correct construct is designated pZMP6/zlmda33.

Example 5

CHO DG44 cells (Chasin et al., *Som. Cell. Molec. Genet.* 12:555–666, 1986) are plated in 10-cm tissue culture dishes and allowed to grow to approximately 50% to 70% confluency overnight at 37° C., 5% CO$_2$, in Ham's F12/FBS media Ham's F12 medium (Life Technologies), 5% fetal bovine serum (Hyclone, Logan, Utah), 1% L-glutamine (JRH Biosciences, Lenexa, Kans.), 1% sodium pyruvate (Life Technologies)). The cells are then transfected with the plasmid zlmda33/pZMP6 by liposome-mediated transfection using a 3:1 (w/w) liposome formulation of the polycationic lipid 2,3-dioleyloxy-N-[2(sperminecarboxamido) ethyl]-N,N-dimethyl-1-propaniminium-trifluoroacetate and the neutral lipid dioleoyl phosphatidylethanolamine in membrane-filetered water (Lipofectamine™ Reagent, Life Technologies), in serum free (SF) media formulation (Ham's F12, 10 mg/ml transferrin, 5 mg/ml insulin, 2 mg/ml fetuin, 1% L-glutamine and 1% sodium pyruvate). pZMP6/zlmda33 is diluted into 15-ml tubes to a total final volume of 640 $\mu$l with SF media. 35 $\mu$l of Lipofectamine™ is mixed with 605 $\mu$l of SF medium. The resulting mixture is added to the DNA mixture and allowed to incubate approximately 30 minutes at room temperature. Five ml of SF media is added to the DNA:Lipofectamine™ mixture. The cells are rinsed once with 5 ml of SF media, aspirated, and the DNA:Lipofectamine™ mixture is added. The cells are incubated at 37° C. for five hours, then 6.4 ml of Ham's F12/10% FBS, 1% PSN media is added to each plate. The plates are incubated at 37° C. overnight, and the DNA:Lipofectamine™ mixture is replaced with fresh 5% FBS/Ham's media the next day. On day 3 post-transfection, the cells are split into T-175 flasks in growth medium. On day 7 posttransfection, the cells are stained with FITC-anti-CD8 monoclonal antibody (Pharmingen, San Diego, Calif.) followed by anti-FITC-conjugated magnetic beads (Miltenyi Biotec). The CD8-positive cells are separated using commercially available columns (mini-MACS columns; Miltenyi Biotec) according to the manufacturer's directions and put into DMEM/Ham's F12/5% FBS without nucleosides but with 50 nM methotrexate (selection medium).

Cells are plated for subcloning at a density of 0.5, 1 and 5 cells per well in 96-well dishes in selection medium and allowed to grow out for approximately two weeks. The wells are checked for evaporation of medium and brought back to 200 µl per well as necessary during this process. When a large percentage of the colonies in the plate are near confluency, 100 µl of medium is collected from each well for analysis by dot blot, and the cells are fed with fresh selection medium. The supernatant is applied to a nitrocellulose filter in a dot blot apparatus, and the filter is treated at 100° C. in a vacuum oven to denature the protein. The filter is incubated in 625 mM Tris-glycine, pH 9.1, 5mM β-mercaptoethanol, at 65° C., 10 minutes, then in 2.5% non-fat dry milk in Western A Buffer (0.25% gelatin, 50 mM Tris-HCl pH 7.4, 150 mM NaCl, 5 mM EDTA, 0.05% Igepal CA-630) overnight at 4° C. on a rotating shaker. The filter is incubated with the antibody-HRP conjugate in 2.5% non-fat dry milk in Western A buffer for 1 hour at room temperature on a rotating shaker. The filter is then washed three times at room temperature in PBS plus 0.01% Tween 20, 15 minutes per wash. The filter is developed with chemiluminescence reagents (ECL™ direct labelling kit; Amersham Corp., Arlington Heights, Ill.) according to the manufacturer's directions and exposed to film (Hyperfilm ECL, Amersham Corp.) for approximately 5 minutes. Positive clones are trypsinized from the 96-well dish and transferred to 6-well dishes in selection medium for scaleup and analysis by Western blot.

Example 6

Full-length zlmda33 protein is produced in BHK cells transfected with pZMP6/zlmda33 (Example 4). BHK 570 cells (ATCC CRL-10314) are plated in 10-cm tissue culture dishes and allowed to grow to approximately 50 to 70% confluence overnight at 37° C., 5% $CO_2$, in DMEM/FBS medium (DMEM, Gibco/BRL High Glucose; Life Technologies supplemented with 5% fetal bovine serum (Hyclone, Logan, Utah), 1 mM L-glutamine (JRH Biosciences, Lenexa, Kans.), and 1 mM sodium pyruvate (Life Technologies)). The cells are then transfected with pZMP6/zlmda33 by liposome-mediated transfection (using Lipofectamine™; Life Technologies), in serum free (SF) medium (DMEM supplemented with 10 mg/ml transferrin, 5 mg/ml insulin, 2 mg/mil fetuin, 1% L-glutamine and 1% sodium pyruvate). The plasmid is diluted into 15-ml tubes to a total final volume of 640 µl with SF medium. 35 µl of the lipid mixture is mixed with 605 µl of SF medium, and the resulting mixture is allowed to incubate approximately 30 minutes at room temperature. Five milliliters of SF medium is then added to the DNA:lipid mixture. The cells are rinsed once with 5 ml of SF medium, aspirated, and the DNA:lipid mixture is added. The cells are incubated at 37° C. for five hours, then 6.4 mil of DMEM/10% FBS, 1% PSN media is added to each plate. The plates are incubated at 37° C. overnight, and the DNA:lipid mixture is replaced with fresh 5% FBS/DMEM medium the next day. On day 5 post-transfection, the cells are split into T-162 flasks in selection medium (DMEM+5% FBS, 1% L-Gln, 1% sodium pyruvate, 1 µM methotrexate). Approximately 10 days post-transfection, two 150-mm culture dishes of methotrexate-resistant colonies from each transfection are trypsinized, and the cells are pooled and plated into a T-162 flask and transferred to large-scale culture.

Example 7 cDNAs and cDNA libraries from a variety of cells and tissues were screened for zlmda33 sequences by PCR using conventional procedures. Cells and tissues testing positive included fetal brain, spinal cord, testis, prostate smooth muscle cells, thyroid, ovarian tumor, uterine tumor, and bone marrow. A tentative positive signal was found in esophageal tumor. Cells and tissues testing negative included adrenal gland, bladder, brain, cervix, colon, fetal heart, fetal kidney, fetal liver, fetal lung, fetal muscle, fetal skin, heart, kidney, liver, lung, lymph node, mammary gland, melanoma, ovary, pancreas, pituitary, placenta, prostate, rectum, salivary gland, skeletal muscle, small intestine, spleen, stomach, thymus, trachea, uterus, adipocyte, islet, bone, liver tumor, lung tumor, rectal tumor, stomach tumor, and K562 (human chronic myelogenous leukemia), RPMI 1788 (B-cell), W138 (lung fibroblast), CD3+, HaCAT (keratinocyte), HPV (prostate epithelia), HPVS (prostate epithelia), and MG63 (osteosarcoma) cell lines.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An expression vector comprising the following operably linked elements:

a transcription promoter;

a DNA segment encoding a protein comprising residues 1–248 of SEQ ID NO:2 or SEQ ID NO:5; and a transcription terminator.

2. The expression vector of claim 1 further comprising a secretory signal sequence operably linked to the DNA segment.

3. The expression vector of claim 1 wherein the DNA segment comprises nucleotides 174–917 of SEQ ID NO:1.

4. A cultured cell into which has been introduced the expression vector of claim 1, wherein the cell expresses the protein encoded by said DNA segment.

5. A method of making a protein comprising:

culturing the cell of claim under conditions wherein the cell expresses the protein encoded by said DNA segment; and recovering the protein.

6. The method of claim 5 wherein the expression vector further comprises a secretory signal sequence operably linked to the DNA segment and wherein the polypeptide is secreted into and recovered from a medium in which the cell is cultured.

7. A protein produced by the method of claim 5.

8. An isolated polynucleotide comprising nucleotides 1–744 of SEQ ID NO:4 or SEQ ID NO:6.

9. The isolated polynucleotide of claim 8 comprising nucleotides 174–917 of SEQ ID NO:1.

* * * * *

SEQUENCE LISTING

```
<160> NUMBER OF SEQ ID NOS: 6
<210> SEQ ID NO 1
<211> LENGTH: 1485
<212> TYPE: DNA
<213> ORGANISM: Homo sapiens
<220> FEATURE:
<221> NAME/KEY: CDS
<222> LOCATION: (174)...(920)

<400> SEQUENCE: 1
ctcattcttc ttgctcaaat tttccaagct tggctaccac gcaaatgaat ccacccaaac      60
gtcaccaagt ggagcagggt accagtatag gtgcaaaaac accctcaatt ccaggagctc     120
```

-continued

| | |
|---|---|
| cacactgaat tcaggccagt ccctggaacc tccccagttt ggctaccaca caa atg<br>                                                                                 Met<br>                                                                                 1 | 176 |
| aat cca ccc aaa cgt cgc caa gtg gag cag ggt ccc agt aca ggt gca<br>Asn Pro Pro Lys Arg Arg Gln Val Glu Gln Gly Pro Ser Thr Gly Ala<br>               5                     10                    15 | 224 |
| aaa aaa ccc tca att tca gga gct cca cac ctg aat tca tac cag tcc<br>Lys Lys Pro Ser Ile Ser Gly Ala Pro His Leu Asn Ser Tyr Gln Ser<br>        20                    25                        30 | 272 |
| ctg gaa ctt ccc cag aag cag cag gat tct ggc act gag gag ctc atg<br>Leu Glu Leu Pro Gln Lys Gln Gln Asp Ser Gly Thr Glu Glu Leu Met<br> 35                     40                         45 | 320 |
| ata gtc ctg gaa caa ggg aca gaa gtg agg ttg agc ctg gaa gag gtc<br>Ile Val Leu Glu Gln Gly Thr Glu Val Arg Leu Ser Leu Glu Glu Val<br> 50                    55                    60                    65 | 368 |
| atc ctc atc ttg gcc cca gag aca gtg ctg cag ctg acc ctg gag aac<br>Ile Leu Ile Leu Ala Pro Glu Thr Val Leu Gln Leu Thr Leu Glu Asn<br>              70                    75                        80 | 416 |
| aca gtc ctt gtg att gtc cct gag cat gtc ctg agg tca gaa gat ggc<br>Thr Val Leu Val Ile Val Pro Glu His Val Leu Arg Ser Glu Asp Gly<br>                   85                    90                        95 | 464 |
| ctg cag tcc cct gtg cag atc cag tac atc ata cct tcc gtt gat gac<br>Leu Gln Ser Pro Val Gln Ile Gln Tyr Ile Ile Pro Ser Val Asp Asp<br>            100                   105                   110 | 512 |
| ttc agc ttg gag ttc cat gct caa gat gga gac atc tca gac atg aga<br>Phe Ser Leu Glu Phe His Ala Gln Asp Gly Asp Ile Ser Asp Met Arg<br>      115                   120                   125 | 560 |
| aga gag aat gtg cct ttt tca cct gca gaa gaa ggg aag gca gca ccc<br>Arg Glu Asn Val Pro Phe Ser Pro Ala Glu Glu Gly Lys Ala Ala Pro<br>130                  135                   140               145 | 608 |
| ctg tat cag cag ccc ttg atg ata ccc caa gca aac cac atg gct ggg<br>Leu Tyr Gln Gln Pro Leu Met Ile Pro Gln Ala Asn His Met Ala Gly<br>               150                   155                   160 | 656 |
| atc agc cct tct ttc cta gta acc cca ttg tgc att cca cgc tgt cgg<br>Ile Ser Pro Ser Phe Leu Val Thr Pro Leu Cys Ile Pro Arg Cys Arg<br>           165                   170                   175 | 704 |
| gca gcc ttc ccc caa tgc tac cct cta cca ccc aca cct agt ccc gtg<br>Ala Ala Phe Pro Gln Cys Tyr Pro Leu Pro Pro Thr Pro Ser Pro Val<br>        180                   185                   190 | 752 |
| gga cgc cct aga cca gcc gac tcc agt ttc agc ctg cat ggt atg gag<br>Gly Arg Pro Arg Pro Ala Asp Ser Ser Phe Ser Leu His Gly Met Glu<br> 195                  200                   205 | 800 |
| ctc ttg tgc acc tcc tcc ctc aga cct atg ccc cct tca cca agt cct<br>Leu Leu Cys Thr Ser Ser Leu Arg Pro Met Pro Pro Ser Pro Ser Pro<br>210                  215                   220               225 | 848 |
| ggt ccc cag gtc tat cac agg gtt cac cat agg cct ccc agc agg gca<br>Gly Pro Gln Val Tyr His Arg Val His His Arg Pro Pro Ser Arg Ala<br>               230                   235                   240 | 896 |
| cgg aga tgt ctc ttt agg aag tga tttaacccaa gagccacccc ctgcattgat<br>Arg Arg Cys Leu Phe Arg Lys *<br>        245 | 950 |
| aggtcagaga ttgtccagat ccttagtcag tgcattctct gaaatgtgga gagaaagtaa | 1010 |
| tttgaccact tgcttgccct ttgctgttcc ccatcatcaa ccactgtctt caacagcgga | 1070 |
| gggtcccaga tgctgcaggg aggggagaa ctgcagggag ttcaaataaa acattccacat | 1130 |
| ttcacttcac acacactgtc ccttagactt tctcttccta tttaagcaca tacatccaac | 1190 |
| cacactcaat caaatccctg actgctccat gtgagagttc tgcttccagc atgacgtggt | 1250 |
| ctgaaagttc atctgaagac agctgctcac tcccgggggc taacaccacc ccttgcatgc | 1310 |

```
tgatgtcctt gtagtcattg gtctgatgcc acaataaata attcctaagg ctgatgctct   1370
atttctgccc tgagactctc ccctttttct ccaagctgtg ccccattcct tgtcttagtc   1430
caggttccct acactcccca ggccaatgct tttgaataaa tcttgacgtc attga        1485
```

```
<210> SEQ ID NO 2
<211> LENGTH: 248
<212> TYPE: PRT
<213> ORGANISM: Homo sapiens

<400> SEQUENCE: 2

Met Asn Pro Pro Lys Arg Arg Gln Val Glu Gln Gly Pro Ser Thr Gly
 1               5                  10                  15

Ala Lys Lys Pro Ser Ile Ser Gly Ala Pro His Leu Asn Ser Tyr Gln
                20                  25                  30

Ser Leu Glu Leu Pro Gln Lys Gln Gln Asp Ser Gly Thr Glu Glu Leu
            35                  40                  45

Met Ile Val Leu Glu Gln Gly Thr Glu Val Arg Leu Ser Leu Glu Glu
        50                  55                  60

Val Ile Leu Ile Leu Ala Pro Glu Thr Val Gln Leu Thr Leu Glu
65                  70                  75                  80

Asn Thr Val Leu Val Ile Val Pro Glu His Val Leu Arg Ser Glu Asp
                85                  90                  95

Gly Leu Gln Ser Pro Val Gln Ile Gln Tyr Ile Ile Pro Ser Val Asp
            100                 105                 110

Asp Phe Ser Leu Glu Phe His Ala Gln Asp Gly Asp Ile Ser Asp Met
        115                 120                 125

Arg Arg Glu Asn Val Pro Phe Ser Pro Ala Glu Glu Gly Lys Ala Ala
130                 135                 140

Pro Leu Tyr Gln Gln Pro Leu Met Ile Pro Gln Ala Asn His Met Ala
145                 150                 155                 160

Gly Ile Ser Pro Ser Phe Leu Val Thr Pro Leu Cys Ile Pro Arg Cys
                165                 170                 175

Arg Ala Ala Phe Pro Gln Cys Tyr Pro Leu Pro Pro Thr Pro Ser Pro
            180                 185                 190

Val Gly Arg Pro Arg Pro Ala Asp Ser Ser Phe Ser Leu His Gly Met
        195                 200                 205

Glu Leu Leu Cys Thr Ser Ser Leu Arg Pro Met Pro Pro Ser Pro Ser
    210                 215                 220

Pro Gly Pro Gln Val Tyr His Arg Val His His Arg Pro Pro Ser Arg
225                 230                 235                 240

Ala Arg Arg Cys Leu Phe Arg Lys
                245

<210> SEQ ID NO 3
<211> LENGTH: 6
<212> TYPE: PRT
<213> ORGANISM: Artificial Sequence
<220> FEATURE:
<223> OTHER INFORMATION: peptide tag

<400> SEQUENCE: 3

Glu Tyr Met Pro Met Glu
 1               5

<210> SEQ ID NO 4
<211> LENGTH: 744
```

```
<212> TYPE: DNA
<213> ORGANISM: Artificial Sequence
<220> FEATURE:
<223> OTHER INFORMATION: degenerate nucleotide sequence
<221> NAME/KEY: misc_feature
<222> LOCATION: (1)...(744)
<223> OTHER INFORMATION: n = A,T,C or G

<400> SEQUENCE: 4
atgaayccnc cnaarmgnmg ncargtngar carggnccnw snacnggngc naaraarccn      60
wsnathwsng gngcnccnca yytnaaywsn taycarwsny tngarytncc ncaraarcar     120
cargaywsng gnacngarga rytnatgath gtnytngarc arggnacnga rgtnmgnytn     180
wsnytngarg argtnathyt nathytngcn ccngaracng tnytncaryt nacnytngar     240
a

```
Val Gly Arg Pro Arg Pro Ala Asp Ser Ser Phe Ser Leu His Gly Met
        195                 200                 205
Glu Leu Leu Cys Thr Ser Ser Leu Arg Pro Met Pro Pro Ser Pro Ser
    210                 215                 220
Pro Gly Pro Gln Val Tyr His Arg Val His His Arg Pro Pro Ser Arg
225                 230                 235                 240
Ala Arg Arg Cys Leu Phe Arg Lys
                245
```

<210> SEQ ID NO 6
<211> LENGTH: 744
<212> TYPE: DNA
<213> ORGANISM: Artificial Sequence
<220> FEATURE:
<223> OTHER INFORMATION: degenerate nucleotide sequence
<221> NAME/KEY: misc_feature
<222> LOCATION: (1)...(744)
<223> OTHER INFORMATION: n = A,T,C or G

<400> SEQUENCE: 6

```
atgaayccnc cnaarmgnmg ncargtngar carggnccnw snacnggngc naaraarccn      60
wsnathwsng gngcnccnca yytnaaywsn taycarwsny tngarytncc ncaraarcar     120
cargaywsng gnacngarga rytnatgath gtnytngarc arggnacnga rgtnmgnytn     180
wsnytngarg argtnathyt nathytngcn ccngaracng tnytncaryt nacnytngar     240
aayacngtny tngarathgt nccngarcay gtnytnmgnw sngargaygg nytncarwsn     300
ccngtncara thcartayat hathccnwsn athgaygayt tywsnytnga rttycaygcn     360
cargayggng ayathwsnga yatgmgnmgn garaaygtnc cnttywsncc ngcngargar     420
ggnaargcng cnccnytnta ycarcarccn ytnatgathc cncargcnaa ycayatggcn     480
ggnathwsnc cnwsnttyyt ngtnacnccn ytntgyathc cnmgntgymg ngcngcntty     540
ccncartgyt ayccnytncc nccnacnccn wsnccngtng gnmgnccnmg nccngcngay     600
wsnwsnttyw snytncaygg natggarytn ytntgyacnw snwsnytnmg nccnatgccn     660
ccnwsnccnw snccnggncc ncargtntay caymgngtnc aycaymgncc nccnwsnmgn     720
gcnmgnmgnt gyytnttymg naar                                            744
```